(12) United States Patent
Piletz et al.

(10) Patent No.: US 7,384,752 B2
(45) Date of Patent: Jun. 10, 2008

(54) DNA ENCODING A HUMAN IMIDAZOLINE RECEPTOR AND LIGAND BINDING ASSAY EMPLOYING SAME

(75) Inventors: John E. Piletz, Madison, MS (US); Tina R. Ivanov, Manchester (GB)

(73) Assignee: University of Mississippi Medical Center, Jackson, MS (US)

( * ) Notice: Subject to any disclaimer, the term of this patent is extended or adjusted under 35 U.S.C. 154(b) by 480 days.

(21) Appl. No.: 10/421,763

(22) Filed: Apr. 24, 2003

(65) Prior Publication Data
US 2003/0224429 A1 Dec. 4, 2003

Related U.S. Application Data

(62) Division of application No. 09/389,487, filed on Sep. 3, 1999, now Pat. No. 6,576,742, which is a division of application No. 08/650,766, filed on May 20, 1996, now Pat. No. 6,015,690.

(60) Provisional application No. 60/012,600, filed on Mar. 1, 1996.

(51) Int. Cl.
*G01N 33/554* (2006.01)
*G01N 33/556* (2006.01)

(52) U.S. Cl. ..................... 435/7.1; 435/7.2; 435/7.21; 436/501

(58) Field of Classification Search ..................... None
See application file for complete search history.

(56) References Cited

OTHER PUBLICATIONS

P. Ernsberger, et al., "Role of Imidazole Receptors in the Vasodepressor Response to Clonidine Analogs in the Rostral Ventrolateral Medulla", The Journal of Pharmacology and Experimental Therapeutics, vol. 253, No. 1, pp. 408-418, 1990.
J. Piletz, et al., Nonadrenergic Imidazoline Binding Sites on Human Platelets, The Journal of Pharmacology and Experimental Therapeutics, vol. 267, No. 3, pp. 1493-1502, 1993.
B. Lanier, et al., "Structural and Ligand Recognition Properties of Imidazoline Binding Proteins in Tissues of Rat and Rabbit", The Journal of Pharmacology and Experimental Therapeutics, vol. 48, pp. 703-710, 1995.
F. Bennai, et al., "Antiidiotypic Antibodies as Tools to Study Imidazoline Receptors", Annals New York Academy of Sciences, vol. 763, pp. 140-148, 1995.
H. Wang, et al., "Isolation and Characterization of Imidazoline Receptor Protien from Bovine Adrenal Chromaffin Cells", The Journal of Pharmacology and Experimental Therapeutics, vol. 42, pp. 792-801, 1992.
H. Wang, et al., "Production and Characterization of Antibodies Specific for the Imidazoline Receptor Protein", The Journal of Pharmacology and Experimental Therapeutics, vol. 43, pp. 509-515, 1993.
P. Ernsberger, et al., "I[1]-Imidazoline Receptors Definition, Characterization, and Transmembrane Signaling", Annals New York Academy of Sciences, vol. 763, pp. 22-42, 1995.

Fourth IBRO World Congress Neuroscience. Abstract G2.29, Piletz, et al., "Platelet $\alpha^2$ and 1[1]-Imdizoline Binding Sites in Depression" Kyoto, Japan, Jul. 9-14, 1995.
J. Piletz, et al., "Imidazoline Receptors in Depression", American College of Neuropsychopharmacology 34th Annual Meeting, p. 119, 1995.
A. Parini, et al., The Elusive Family of Imidazoline Binding Sites, TiPS, vol. 17, pp. 13-16, 1996.
J. Piletz, et al., Desipramine Lowers Tritiated Para-Aminoclonidine Binding in Platelets of Depressed Patients, Arch Gen Psychiatry, vol. 408, pp. 813-820, 1991.
J. Piletz, et al., "Psychopharmacology of Imidazoline and $\alpha$2-Adrenergic Recpetors: Implications for Depression", Critical Reviews in Neurobiology, vol. 9, No. 1, pp. 26-66, 1994.
EST04033, in : Adams, et al., Nature Genet, 4, pp. 256-267.
Lin, et al., Science, vol. 190, pp. 61-63, 1975.
P. Ernsberger et al., "Role of Imidazole Receptors in the Vasodepressor Response to Clonidine Analogs in the Rostral Ventrolateral Medulla[1]", The Journal of Pharmacology and Experimental Therapeutics, vol. 253, No. 1, pp. 408-418, (1990).
J. Piletz et al., "Nonadrenergic Imidazoline Binding Sites on Human Platelets", The Journal of Pharmacology and Experimental Therapeutics, vol. 267, No. 3, pp. 1493-1502, (1993).
B. Lanier et al., "Structural and Ligand Recognition Properties of Imidazoline Binding Proteins in Tissues of Rat and Rabbit", The American Society for Pharmacology and Experimental Therapeutics, vol. 48, pp. 703-710, (1995).
F. Bennai et al., "Antiidiotypic Antibodies as Tools to Study Imidazoline Receptors", Annals New York Academy of Sciences, vol. 763, pp. 140-148, (1995).
H. Wang et al., "Isolation and Characterization of Imidazoline Receptor Protein from Bovine Adrenal Chromaffin Cells", The American Society for Pharmacology and Experimental Therapeutics, vol. 42, pp. 792-801, ((1992).
H. Wang et al., "Production and Characterization of Antibodies Specific for the Imidazoline Receptor Protein", The American Society for Pharmacology and Experimental Therapeutics, vol. 43, pp. 509-515, (1993).
P. Ernsberger et al., "I[1]-Imidazoline Receptors Definition, Characterization, Distribution, and Transmembrane Signaling", Annals New York Academy of Sciences, vol. 763, pp. 22-42, (1995).

(Continued)

*Primary Examiner*—John Ulm
(74) *Attorney, Agent, or Firm*—Stites & Harbison PLLC; Richard S. Myers, Jr.; Stephen Weyer

(57) ABSTRACT

A cDNA encoding a human imidazoline receptor is described. The amino acid sequence of the entire imidazoline receptor protein is identified, as well as a C-terminal fragment believed to contain the imidazoline binding site of the receptor. The protein is highly unique in its sequence and may represent the first in a novel family of receptor proteins. Methods of cloning the cDNA and expressing the imidazoline receptor in a host cell are described. Also, a screening method for identifying drugs that interact with the imidazoline receptor is described.

5 Claims, 3 Drawing Sheets

OTHER PUBLICATIONS

Fourth IBRO World Congress of Neuroscience. Abstract G2.29, Piletz et al. Platelet $\alpha^1$- and $1^1$-Imidizoline Binding Sites in Depression, Kyoto, Japan, Jul. 9-14, (1995).

J. Piletz et al., "Imidazoline Receptors in Depression", American College of Neuropsychopharmacology, 34th Annual Meeting, Poster Session 1, p. 119, (1995).

A. Parini et al., "The Elusive Family of Imidazoline Binding Sites", TiPS, vol. 17, pp. 13-16, (1996).

J. Piletz et al., "Desipramine Lowers Tritiated Para-Aminoclonidine Binding in Platelets of Depressed Patients", Arch Gen Psychiatry, vol. 48, pp. 813-820, (1991).

J. Piletz et al., "Psychopharmacology of Imidazoline and $\alpha_2$-Adrenergic Receptors: Implications for Depression", Critical Reviews in Neurobiology, vol. 9, No. 1, pp. 29-66, (1994).

Adams et al., ESTO4033 *Homo sapiens* cDNA, locus TO6144, Jun. 30, 1993.

Wang et al., Molecular Pharmacology 43 (4) 509-515, Apr. 1993.

Lin et al., Science 190:61-63, Oct. 1975.

REIS AB
1:15,000 DILUTION

DONTEWILL AB
1:20,000 DILUTION

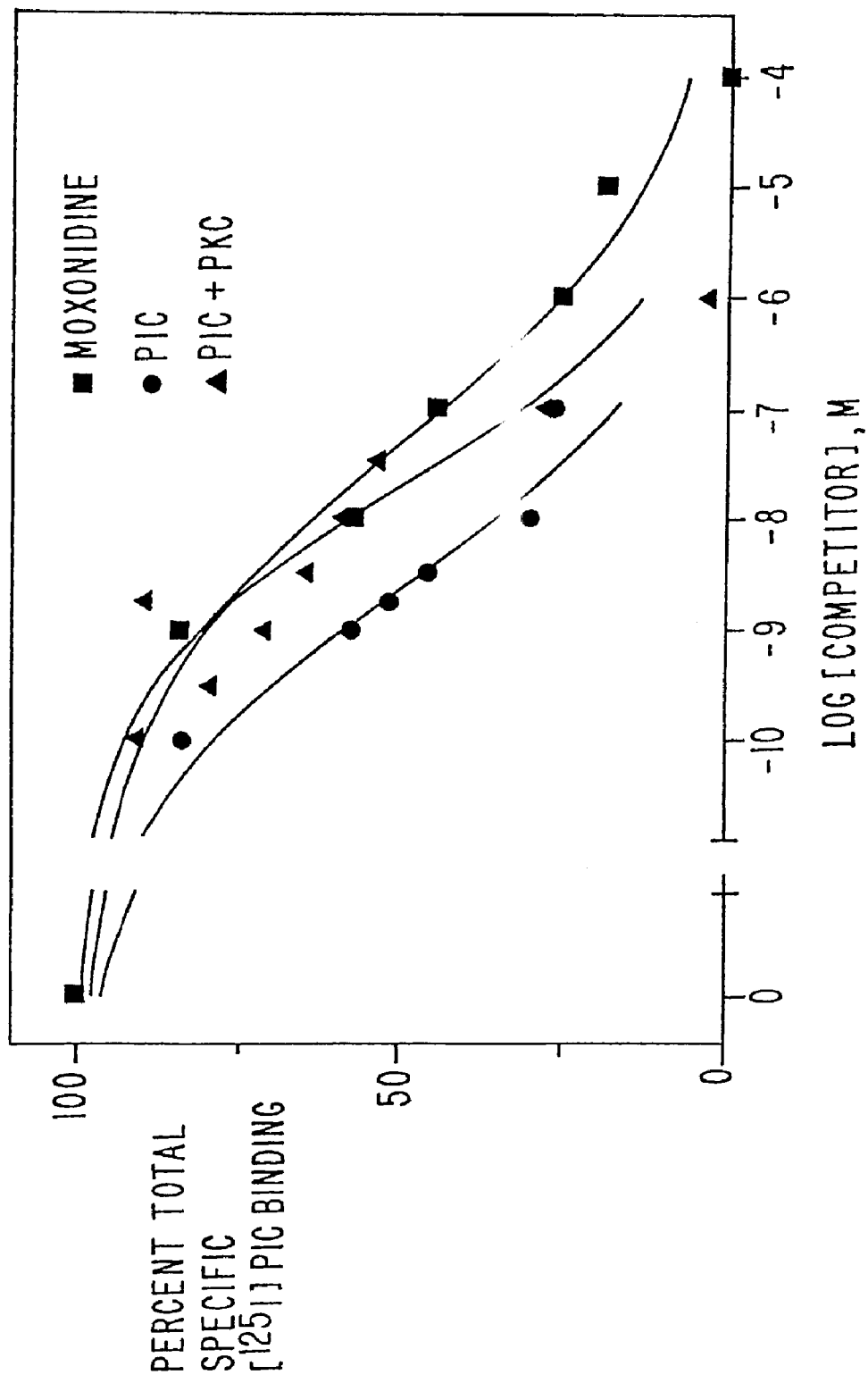

SEQUENCE LISTING

<160> NUMBER OF SEQ ID NOS: 21

<210> SEQ ID NO 1
<211> LENGTH: 3385
<212> TYPE: DNA
<213> ORGANISM: Homo sapiens
<220> FEATURE:
<221> NAME/KEY: CDS
<222> LOCATION: (1398)..(3383)

<400> SEQUENCE: 1

```
        gctctagaac tagtggatcc cccgggctgc aggaattcca gtttaatact aaccctaatg     60
        tgtgactgcg gtttacaaag agctctgtat cacctgggat agctttcagt agcaattcac    120
        tacaactggt cctaaaaaat aataacaata ataataataa ttagagaatt aaaacccaac    180
        agcatgttga atggttaaaa tcacgtaaga actgaaattt ggggtggggg tgtcctcaac    240
        agctgagctt gtcctagcag tgaaaatgct cgcctccaag cagggctcag aaaggtctgg    300
        agccctccag gcagagggct gagctcaggg ggctcttgga ggacactcac cccatgtcc    360
        atgggatgct tctggcttcc ttaaaaacag ttgggcatcc gcattgtata agtaggtgga    420
        gaccctagtg tggttctttt gaaggatatg ggaagggagg atgacgaact agagaagtgg    480
        gaggggacca aaatcactga ggtcccagaa tatcatagat ttgggtatag gattggggtc    540
        actaagaatt gagcaccagg aattccagct tcttcccatt aaagaaactg ggactggttt    600
        tgccttggag gcctatgtag tgtttctgc ccctgtccca taccaagtct cattgatatt    660
        tctgcagaat atcagatgaa aatctatttc taaagaccat tgggagaatg ggtggtggag    720
        aaggagttgg agtggggttg ggggggcagtt aaaaatgaat aaaaatctct cagctacaga    780
        acccaaacat cacttccctc cgcattcaca gcatttccca gcagtcccca gatggttgtt    840
        tccgtgggga cacagcagct gcctcatttc ccttcaggcc ccatgggctg ctggtcaacc    900
        tcaggatcta ctaaagatga cgcaaatgcc gactgaacaa tctgaaaccc aaaggactcg    960
        aggagagaca tgttctgctg aggagagaaa ggtgagccaa gggcagggcc caggtccccc   1020
        aggggggcccc cgagagcccg gacatgcacc ttctggatgt gttttgttcaa gtaggactta   1080
        gagcggaaga agctcccaca ttcagggcat gggtacttct tctccccatc agactccatt   1140
        ttgttttttgg ggactgccat gtcgcaggag aaagagccat tggcactctg ctttctctggc   1200
        gtcttcaggt cgctggcatc tgagaggtca ccataggagt cagagctctc aatcggatcc   1260
        tgatgtgagc atttctggcc ttctcggtta cagatactgc agaagttgct gggcccctcg   1320
        ctgtgcttct tcaggtggtc tgccatgtat gctgcccgca agtacttccc acacacctgg   1380
        cagggcacct tgtcttc atg aca ggc cag gtg gga gcg cag acg gtc tcg        1430
                        Met Thr Gly Gln Val Gly Ala Gln Thr Val Ser
                         1               5                  10
        ggt ggc aaa aga agc att gca ggt ctg aca ctt gtg agg ccg ctc aga      1478
        Gly Gly Lys Arg Ser Ile Ala Gly Leu Thr Leu Val Arg Pro Leu Arg
                 15                  20                  25
        agt gtg cac ctg ctt gat atg tcc gtt caa gtg atc agg cct gga gaa      1526
        Ser Val His Leu Leu Asp Met Ser Val Gln Val Ile Arg Pro Gly Glu
             30                  35                  40
        gcc ttt ccc aca gct ctg gca gat gta agg cgg aat tcc cca gag aag      1574
        Ala Phe Pro Thr Ala Leu Ala Asp Val Arg Arg Asn Ser Pro Glu Lys
         45                  50                  55
        aag ggt ggt gaa gac tcc cgg ctc tca gct gcc ccc tgc atc aga ccc      1622
        Lys Gly Gly Glu Asp Ser Arg Leu Ser Ala Ala Pro Cys Ile Arg Pro
         60                  65                  70                  75
        agc agc tcc cct ccc act gtg gct ccc gca tct gcc tcc ctg ccc cag      1670
        Ser Ser Ser Pro Pro Thr Val Ala Pro Ala Ser Ala Ser Leu Pro Gln
                     80                  85                  90
        ccc atc ctc tct aac caa gga atc atg ttc gtt cag gag gag gcc ctg      1718
        Pro Ile Leu Ser Asn Gln Gly Ile Met Phe Val Gln Glu Glu Ala Leu
                 95                 100                 105
        gcc agc agc ctc tcg tcc act gac agt ctg act ccc gag cac cag ccc      1766
        Ala Ser Ser Leu Ser Ser Thr Asp Ser Leu Thr Pro Glu His Gln Pro
             110                 115                 120
        att gcc cag gga tgt tct gat tcc ttg gag tcc atc cct gcg gga cag      1814
        Ile Ala Gln Gly Cys Ser Asp Ser Leu Glu Ser Ile Pro Ala Gly Gln
         125                 130                 135
```

-continued

```
gca gct tcc gat gat tta agg gac gtg cca gga gct gtt ggt ggt gca    1862
Ala Ala Ser Asp Asp Leu Arg Asp Val Pro Gly Ala Val Gly Gly Ala
140             145                 150                 155
agc cca gaa cat gcc gag ccg gag gtc cag gtg gtg ccg ggg tct ggc    1910
Ser Pro Glu His Ala Glu Pro Glu Val Gln Val Val Pro Gly Ser Gly
            160                 165                 170
cag atc atc ttc ctg ccc ttc acc tgc att ggc tac acg gcc acc aat    1958
Gln Ile Ile Phe Leu Pro Phe Thr Cys Ile Gly Tyr Thr Ala Thr Asn
        175                 180                 185
cag gac ttc atc cag cgc ctg agc aca ctg atc cgg cag gcc atc gag    2006
Gln Asp Phe Ile Gln Arg Leu Ser Thr Leu Ile Arg Gln Ala Ile Glu
    190                 195                 200
cgg cag ctg cct gcc tgg atc gag gct gcc aac cag cgg gag gag ggc    2054
Arg Gln Leu Pro Ala Trp Ile Glu Ala Ala Asn Gln Arg Glu Glu Gly
205                 210                 215
cag ggt gaa cag ggc gag gag gag gat gag gag gaa gaa gag gag        2102
Gln Gly Glu Gln Gly Glu Glu Glu Asp Glu Glu Glu Glu Glu Glu
220                 225                 230                 235
gac gtg gct gag aac cgc tac ttt gaa atg ggg ccc cca gac gtg gag    2150
Asp Val Ala Glu Asn Arg Tyr Phe Glu Met Gly Pro Pro Asp Val Glu
                240                 245                 250
gag gag gag gga gga ggc cag ggg gag gaa gag gag gaa gag gag        2198
Glu Glu Glu Gly Gly Gly Gln Gly Glu Glu Glu Glu Glu Glu Glu
            255                 260                 265
gat gaa gag gcc gag gag gag cgc ctg gct ctg gaa tgg gcc ctg ggc    2246
Asp Glu Glu Ala Glu Glu Glu Arg Leu Ala Leu Glu Trp Ala Leu Gly
        270                 275                 280
gcg gac gag gac ttc ctg ctg gag cac atc cgc atc ctc aag gtg ctg    2294
Ala Asp Glu Asp Phe Leu Leu Glu His Ile Arg Ile Leu Lys Val Leu
    285                 290                 295
tgg tgc ttc ctg atc cat gtg cag ggc agt atc cgc cag ttc gcc gcc    2342
Trp Cys Phe Leu Ile His Val Gln Gly Ser Ile Arg Gln Phe Ala Ala
300                 305                 310                 315
tgc ctt gtg ctc acc gac ttc ggc atc gca gtc ttc gag atc ccg cac    2390
Cys Leu Val Leu Thr Asp Phe Gly Ile Ala Val Phe Glu Ile Pro His
                320                 325                 330
cag gag tct cgg ggc agc agc cag cac atc ctc tcc tcc ctg cgc ttt    2438
Gln Glu Ser Arg Gly Ser Ser Gln His Ile Leu Ser Ser Leu Arg Phe
            335                 340                 345
gtc ttt tgc ttc ccg cat ggc gac ctc acc gag ttt ggc ttc ctc atg    2486
Val Phe Cys Phe Pro His Gly Asp Leu Thr Glu Phe Gly Phe Leu Met
        350                 355                 360
ccg gag ctg tgt ctg gtg ctc aag gta cgg cac agt gag aac acg ctc    2534
Pro Glu Leu Cys Leu Val Leu Lys Val Arg His Ser Glu Asn Thr Leu
365                 370                 375
ttc att atc tcg gac gcc gcc aac ctg cac gag ttc cac gcg gac ctg    2582
Phe Ile Ile Ser Asp Ala Ala Asn Leu His Glu Phe His Ala Asp Leu
380                 385                 390                 395
cgc tca tgc ttt gca ccc cag cac atg gcc atg ctg tgt agc ccc atc    2630
Arg Ser Cys Phe Ala Pro Gln His Met Ala Met Leu Cys Ser Pro Ile
                400                 405                 410
ctc tac ggc agc cac acc agc ctg cag gag ttc ctg cgc cag ctg ctc    2678
Leu Tyr Gly Ser His Thr Ser Leu Gln Glu Phe Leu Arg Gln Leu Leu
            415                 420                 425
acc ttc tac aag gtg gct ggc ggc tgc cag gag cgc agc cag ggc tgc    2726
Thr Phe Tyr Lys Val Ala Gly Gly Cys Gln Glu Arg Ser Gln Gly Cys
        430                 435                 440
ttc ccc gtc tac ctg gtc tac agt gac aag cgc atg gtg cag acg gcc    2774
Phe Pro Val Tyr Leu Val Tyr Ser Asp Lys Arg Met Val Gln Thr Ala
    445                 450                 455
gcc ggg gac tac tca ggc aac atc gag tgg gcc agc tgc aca ctc tgt    2822
Ala Gly Asp Tyr Ser Gly Asn Ile Glu Trp Ala Ser Cys Thr Leu Cys
460                 465                 470                 475
tca gcc gtg cgg cgc tcc tgc tgc gcg ccc tct gag gcc gtc aag tcc    2870
Ser Ala Val Arg Arg Ser Cys Cys Ala Pro Ser Glu Ala Val Lys Ser
                480                 485                 490
gcc gcc atc ccc tac tgg ctg ttg ctc acg ccc cag cac ctc aac gtc    2918
Ala Ala Ile Pro Tyr Trp Leu Leu Leu Thr Pro Gln His Leu Asn Val
            495                 500                 505
atc aag gcc gac ttc aac ccc atg ccc aac cgt ggc acc cac aac tgt    2966
Ile Lys Ala Asp Phe Asn Pro Met Pro Asn Arg Gly Thr His Asn Cys
        510                 515                 520
cgc aac cgc aac agc ttc aag ctc agc cgt gtg ccg ctc tcc acc gtg    3014
Arg Asn Arg Asn Ser Phe Lys Leu Ser Arg Val Pro Leu Ser Thr Val
    525                 530                 535
ctg ctg gac ccc aca cgc agc tgt acc cag cct cgg ggc gcc ttt gct    3062
Leu Leu Asp Pro Thr Arg Ser Cys Thr Gln Pro Arg Gly Ala Phe Ala
540                 545                 550                 555
gat ggc cac gtg cta gag ctg ctc gtg ggg tac cgc ttt gtc act gcc    3110
```

```
        Asp Gly His Val Leu Glu Leu Leu Val Gly Tyr Arg Phe Val Thr Ala
                        560                 565                 570
        atc ttc gtg ctg ccc cac gag aag ttc cac ttc ctg cgc gtc tac aac   3158
        Ile Phe Val Leu Pro His Glu Lys Phe His Phe Leu Arg Val Tyr Asn
                    575                 580                 585
        cag ctg cgg gcc tcg ctg cag gac ctg aag act gtg gtc atc gcc aag   3206
        Gln Leu Arg Ala Ser Leu Gln Asp Leu Lys Thr Val Val Ile Ala Lys
                590                 595                 600
        acc ccc ggg acg gga ggc agc ccc cag ggc tcc ttt gcg gat ggc cag   3254
        Thr Pro Gly Thr Gly Gly Ser Pro Gln Gly Ser Phe Ala Asp Gly Gln
            605                 610                 615
        cct gcc gag cgc agg gcc agc aat gac cag cgt ccc cag gag gtc cca   3302
        Pro Ala Glu Arg Arg Ala Ser Asn Asp Gln Arg Pro Gln Glu Val Pro
        620                 625                 630                 635
        gca gag gct ctg gcc ccg gcc cca gtg gaa gtc cca gct cca gcc ccg   3350
        Ala Glu Ala Leu Ala Pro Ala Pro Val Glu Val Pro Ala Pro Ala Pro
                        640                 645                 650
        gaa ttc gat atc aag ctt atc gat acc gtc gac ct                    3385
        Glu Phe Asp Ile Lys Leu Ile Asp Thr Val Asp
                        655                 660
```

<210> SEQ ID NO 2
<211> LENGTH: 1678
<212> TYPE: DNA
<213> ORGANISM: Homo sapiens

<400> SEQUENCE: 2

```
    atgacaggcc aggtgggagc gcagacggtc tcgggtggca aaagaagcat tgcaggtctg   60
    acacttgtga ggccgctcag aagtgtgcac ctgcttgata tgtccgttca agtgatcagg  120
    cctggagaag cctttcccac agctctggca gatgtaaggc ggaattcccc agagaagaag  180
    ggtggtgaga actcccggct ctcagctgcc ccctgcatca gacccagcag ctcccctccc  240
    actgtggctc ccgcatctgc ctccctgccc cagcccatcc tctctaacca aggaatcatg  300
    ttcgttcagg aggaggccct ggccagcagc ctctcgtcca ctgacagtct gactcccgag  360
    caccagccca tgcccaggg atgttctgat tccttggagt ccatccctgc gggacaggca  420
    gcttccgatg atttaaggga cgtgccagga gctgttggtg gtgcaagccc agaacatgcc  480
    gagccggagg tccaggtggt gccggggtct ggccagatca tcttcctgcc cttcacctgc  540
    attggctaca cggccaccaa tcaggacttc atccagcgcc tgagcacact gatccggcag  600
    gccatcgagc ggcagctgcc tgcctggatc gaggctgcca accagcggga ggagggccag  660
    ggtgaacagg gcgaggagga ggatgaggag gaggaagaag aggaggacag ggctgagaac  720
    cgctactttg aaatgggggcc cccagacgtg gaggaggagg agggaggagg ccaggggggag  780
    gaagaggagg aggaagagga ggatgaagag gccgaggagg agcgcctggc tctggaatgg  840
    gccctgggcg cggacgagga cttcctgctg agcacatcc gcatcctcaa ggtgctgtgg  900
    tgcttcctga tccatgtgca gggcagtatc cgccagttcg ccgcctgcct tgtgctcacc  960
    gacttcggca tcgcagtctt cgagatcttg caccaggact ccggggcag cagccagcac 1020
    atcctctcct ccctgcgctt tgtctttgc ttcccgcatg gcgacctcac cgagtttggc 1080
    ttcctcatgc cggagctgtg tctggtgctc aaggtacggg acagtgagaa cacgctcttc 1140
    attatctcgg acgccgccaa cctgcacgag ttccacgcgg acctgcgctc atgctttgca 1200
    ccccagcaca tggccatgct tgtgtagccc atcctctacg gcagccacac cagcctgcag 1260
    gagttcctgc gccagctgct caccttctac aaggtggctg gcggctgcca ggagcgcagc 1320
    cagggctgct tccccgtcta cctggtctac agtgacaagc gcatggtgca gacggccgcc 1380
    ggggactact caggcaacat cgagtgggcc agctgcacac tctgttcagc cgtgcggcgc 1440
    tcctgctgcg cgccctctga ggccgtcaag tccgccgaca tccctactg gctgttgctc 1500
    acgccccagc acctcaacgt catcaaggcc gacttcaacc ccatgcccaa ccgtgggacc 1560
    cacaactgtc gcaaccgcaa cagcttcaag ctcagccgtg tgccgctctc accgtgctg 1620
    ctggacccca cacgcagctg tacccagcct cgggcgcct tgctgatgg ccacgtgc    1678
```

<210> SEQ ID NO 3
<211> LENGTH: 3318
<212> TYPE: DNA
<213> ORGANISM: Homo sapiens

<400> SEQUENCE: 3

```
    aattccagtt taatactaac cctaatgtgt gactgcggtt tacaaagagc tctgtatcac   60
    ctgggatagc tttcagtagc aattcactac aactggtcct aaaaaataat aacaataata  120
    ataataatta gagaattaaa acccaacagc atgttgaatg gttaaaatca cgtaagaact  180
    gaaatttggg gtgggggtgt cctcaacagc tgagcttgtc ctagcagtga aaatgctcgc  240
    ctccaagcag ggctcagaaa ggtctggagc cctccaggca gagggctgag ctcaggggag  300
    tcttggagga cactcacccc atggtccatg ggatgcttct ggcttcctta aaaacagttg  360
    ggcatccgca ttgtataagt aggtggagac cctagtgtgg ttcttttgaa ggatatggga  420
    agggaggatg acgaactaga gaagtggag gggaccaaaa tcactgaggt cccagaatat  480
    catagatttg ggtataggat tggggtcact aagaattgag caccaggaat tccagcttct  540
    tcccattaaa gaaactggga ctggttttgc cttggaggcc tatgtagtgt tttctgcccc  600
    tgtcccatac caagtctcat tgatatttct gcagaatatc agatgaaaat ctatttctaa  660
    agaccattgg gagaatgggt ggtgagaag gagttggagt ggggttgggg ggcagttaaa  720
    aatgaataaa aatctctcag ctacagaacc caaacatcac ttccctccgc attcacagca  780
```

```
tttcccagca gtccccagat ggttgtttcc gtggggacac agcagctgcc tcatttccct   840
tcaggcccca tgggctgctg gtcaacctca ggatctacta aagatgacgc aaatgccgac   900
tgaacaatct gaaacccaaa ggactcgagg agagacatgt tctgctgagg agagaaaggt   960
gagccaaggg cagggcccag gtcccccaagg ggccccccga gagcccggac atgcaccttc  1020
tggatgtgtt tgttcaagta ggacttagag cggaagaagc tcccacattc agggcatggg  1080
tacttcttct ccccatcaga ctccatttg tttttgggga ctgccatgtc gcaggagaaa   1140
gagccattgg cactctgctt ctctggcgtc ttcaggtcgc tggcatctga gaggtcacca  1200
taggagtcag agctctcaat cggatcctga tgtgagcatt tctggccttc tcggttacag  1260
atactgcaga agttgctggg cccctcgctg tgcttcttca ggtggtctgc catgtatgct  1320
gcccgcaagt acttcccaca cacctggcag ggcaccttgt cttcatgaca ggccaggtgg  1380
gagcgcagac ggtctcgggt ggcaaaagaa gcattgcagg tctgacactt gtgaggccgc  1440
tcagaagtgt gcacctgctt gatatgtccg ttcaagtgat caggcctgga gaagccttc   1500
ccacagctct ggcagatgta aggcggaatt ccccagagaa gaagggtggt gaagactccc  1560
ggctctcagc tgcccctgc atcagaccca gcagctcccc tcccactgtg gctcccgcat   1620
ctgcctccct gccccagccc atcctctcta accaaggaat catgttcgtt caggaggagg  1680
ccctggccag cagcctctcg tccactgaca gtctgactcc cgagcaccag cccattgccc  1740
agggatgttc tgattccttg gagtccatcc ctgcgggaca ggcagcttcc gatgatttaa  1800
gggacgtgcc aggagctgtt ggtggtgcaa gccagaaca tgccgagccg gaggtccagg   1860
tggtgccggg gtctggccag atcatcttcc tgcccttcac ctgcattggc tacacggcca  1920
ccaatcagga cttcatccag cgcctgagca cactgatccg gcaggccatc gagcggcagc  1980
tgcctgcctg gatcgaggct gccaaccagc gggaggaggg ccagggtgaa caggcgcagg  2040
aggaggatga ggaggaggaa gaagaggagg acgtggctga gaaccgctac tttgaaatgg  2100
ggccccagaa cgtggaggag gaggaggagg aggccaggg ggaggaagag gaggaggaag    2160
aggaggatga agaggccgag gaggagcgcg tggctctgga atgggccctg ggcgcggacg  2220
aggacttcct gctggagcac atccgcatcc tcaaggtgct gtggtcctcc ctgatccatg  2280
tgcagggcag tatccgccag ttcgccgcct gccttgtgct caccgacttc ggcatcgcag  2340
tcttcgagat cccgcaccag gagtctcggg gcagcagcca gcacatcctc tcctccctgc  2400
gctttgtctt ttgcttcccg catggcgacc tcaccgagtt tggcttcctc atgccggagc  2460
tgtgtctggt gctcaaggta cggcacagtg agaacacgtc cttcattatc tcggacgccg  2520
ccaacctgca cgagttccac gcggacctgc gctcatgctt tgcaccccag cacatggcca  2580
tgctgtgtag ccccatcctc tacggcagcc acaccagcct gcaggagttc ctgcgccagc  2640
tgctcacctt ctacaaggtg gctggcggct gccaggagcg cagcagggc tgcttccccg   2700
tctacctggt ctacagtgac aagcgcatgg tgcagccgac gtgtgctca tactcaggca   2760
acatcgagtg ggccagctgc acactctgtt cagccgtgcg cgctcctgc tgcgcgccct    2820
ctgaggccgt caagtccgcc gccatcccct actggctgtt gctcacgccc cagcacctca  2880
acgtcatcaa ggccgacttc aaccccatgc caaccgtgg cacccacaac tgtcgcaacc   2940
gcaacagctt caagctcagc cgtgtgccgc tctccaccgt gctgctggac cccacacgca  3000
gctgtaccca gcctcgggc gcctttgctg atggccacgt gctagagctg ctcgtgggt    3060
accgctttgt cactgccatc ttcgtgctgc cccacgagaa gttccactc ctgcgcgtct    3120
acaaccagct gcgggcctcg ctgcaggacc tgaagactgt ggtcatcgcc aagaccccg    3180
ggacgggagg cagccccag ggctcctttg cggatggcca gcctgccgag cgcagggcca   3240
gcaatgacca gcgtccccag gaggtcccag cagaggctct ggccccggcc ccagtggaag  3300
tcccagctcc agccccgg                                                3318
```

<210> SEQ ID NO 4
<211> LENGTH: 895
<212> TYPE: DNA
<213> ORGANISM: Homo sapiens

<400> SEQUENCE: 4

```
gaggaggagg aagaggagga tgaagaggcc gaggaggagc gcctggctct ggaatgggcc   60
ctgggcgcgg acgaggactt cctgctggag cacatccgag tcctcaaggt gctgtggtgc  120
ttcctgatcc atgtgcaggg cagtatccgc cagttcgccg cctgccttgt gctcaccgac  180
ttcggcatcg cagtcttcga gatcccgcac caggagtctc ggggcagcag ccagcacatc  240
ctctcctccc tgcgctttgt cttttgcttc ccgcatggcg acctcaccga gtttggcttc  300
ctcatgccgg agctgtgtct ggtgctcaag gtacggcaca gtgagaacac gctcttcatt  360
atctcggacg ccgccaacct gcacgagttc cacgcggacc tgcgctcatg ctttgcaccc  420
cagcacatgg ccatgctgtg tagccccatc ctctacggca gccacaccag cctgcaggag  480
ttcctgcgcc agctgctcac cttctacaag gtggctggcg gctgccagga gcgcagccag  540
ggctgcttcc ccgtctacct ggtctacagt gacaagcgca tggtgcagac ggccgccggg  600
gactactcag gcaacatcga gtgggccagc tgcacactct gttcagccgt gcgcgctcc   660
tgctgcgcgc cctctgaggc cgtcaagtcc gccgcatcc cctactggct gttgctcacg   720
ccccagcacc tcaacgtcat caaggccgac ttcaacccca tgcccaaccg tggcacccac  780
aactgtcgca accgcaacag cttcaagctc agccgtgtgc cgctctccac cgtgctgctg  840
gaccccacac gcagctgtac ccagcctcgg ggcgcctttg ctgatggcca cgtgc        895
```

<210> SEQ ID NO 5
<211> LENGTH: 1171
<212> TYPE: DNA
<213> ORGANISM: Homo sapiens

<400> SEQUENCE: 5

```
gaggaggagg aagaggagga tgaagaggcc gaggaggagc gcctggctct ggaatgggcc   60
ctgggcgcgg acgaggactt cctgctggag cacatccgca tcctcaaggt gctgtggtgc  120
ttcctgatcc atgtgcaggg cagtatccgc cagttcgccg cctgccttgt gctcaccgac  180
```

-continued

```
ttcggcatcg cagtcttcga gatcccgcac caggagtctc ggggcagcag ccagcacatc 240
ctctcctccc tgcgctttgt cttttgcttc ccgcatggcg acctcaccga gtttggcttc 300
ctcatgccgg agctgtgtct ggtgctcaag gtacggcaca gtgagaaacac gctcttcatt 360
atctcggacg ccgccaacct gcacgagttc cacgcggacc tgcgctcatg ctttgcaccc 420
cagcacatgg ccatgctgtg tagccccatc ctctacggca gccacaccga cctgcaggag 480
ttcctgcgcc agctgctcac cttctacaag gtggctggcg gctgccagga gcgcagccag 540
ggctgcttcc ccgtctacct ggtctacagt gacaagcgca tggtgcagac ggccgccggg 600
gactactcag gcaacatcga gtgggccagc tgcacactct gttcagccgt gcggcgctcc 660
tgctgcgcgc cctctgaggc cgtcaagtcc gccgccatcc cctactggct gttgctcacg 720
ccccagcacc tcaacgtcat caaggccgac ttcaaccccca tgcccaaccg tggcacccac 780
aactgtcgca accgcaacag cttcaagctc agccgtgtgc cgctctccac cgtgctgctg 840
gaccccacac gcagctgtac ccagcctcgg ggcgcctttg ctgatgccca cgtgctagag 900
ctgctcgtgg ggtaccgctt tgtcactgcc atcttcgtgc tgccccacga gaagttccac 960
ttcctgcgcg tctacaacca gctgcgggcc tcgctgcagg acctgaaagac tgtggtcatc 1020
gccaagaccc ccgggacggg aggcagcccc cagggctcct ttgcggatgg ccagcctgcc 1080
gagcgcaggg ccagcaatga ccagcgtccc caggaggtcc cagcagaggc tctggccccg 1140
gccccagtgg aagtcccagc tccagccccg g 1171
```

<210> SEQ ID NO 6
<211> LENGTH: 651
<212> TYPE: PRT
<213> ORGANISM: Homo sapiens

<400> SEQUENCE: 6

```
Met Thr Gly Gln Val Gly Ala Gln Thr Val Ser Gly Gly Lys Arg Ser
 1               5                  10                  15
Ile Ala Gly Leu Thr Leu Val Arg Pro Leu Arg Ser Val His Leu Leu
                20                  25                  30
Asp Met Ser Val Gln Val Ile Arg Pro Gly Glu Ala Phe Pro Thr Ala
            35                  40                  45
Leu Ala Asp Val Arg Arg Asn Ser Pro Glu Lys Lys Gly Gly Glu Asp
        50                  55                  60
Ser Arg Leu Ser Ala Ala Pro Cys Ile Arg Pro Ser Ser Pro Pro
 65                  70                  75                  80
Thr Val Ala Pro Ala Ser Ala Ser Leu Pro Gln Pro Ile Leu Ser Asn
                85                  90                  95
Gln Gly Ile Met Phe Val Gln Glu Ala Leu Ala Ser Ser Leu Ser
                100                 105                 110
Ser Thr Asp Ser Leu Thr Pro Glu His Gln Pro Ile Ala Gln Gly Cys
            115                 120                 125
Ser Asp Ser Leu Glu Ser Ile Pro Ala Gly Gln Ala Ala Ser Asp Asp
        130                 135                 140
Leu Arg Asp Val Pro Gly Ala Val Gly Gly Ala Ser Pro Glu His Ala
145                 150                 155                 160
Glu Pro Glu Val Gln Val Val Pro Gly Ser Gly Gln Ile Ile Phe Leu
                165                 170                 175
Pro Phe Thr Cys Ile Gly Tyr Thr Ala Thr Asn Gln Asp Phe Ile Gln
                180                 185                 190
Arg Leu Ser Thr Leu Ile Arg Gln Ala Ile Glu Arg Gln Leu Pro Ala
            195                 200                 205
Trp Ile Glu Ala Ala Asn Gln Arg Glu Glu Gly Gln Gly Glu Gln Gly
        210                 215                 220
Glu Glu Glu Asp Glu Glu Glu Glu Glu Asp Val Ala Glu Asn
225                 230                 235                 240
Arg Tyr Phe Glu Met Gly Pro Pro Asp Val Glu Glu Glu Gly Gly
                245                 250                 255
Gly Gln Gly Glu Glu Glu Glu Glu Glu Asp Glu Ala Glu
                260                 265                 270
Glu Glu Arg Leu Ala Leu Glu Trp Ala Leu Gly Ala Asp Glu Asp Phe
            275                 280                 285
Leu Leu Glu His Ile Arg Ile Leu Lys Val Leu Trp Cys Phe Leu Ile
        290                 295                 300
His Val Gln Gly Ser Ile Arg Gln Phe Ala Ala Cys Leu Val Leu Thr
305                 310                 315                 320
Asp Phe Gly Ile Ala Val Phe Glu Ile Pro His Gln Glu Ser Arg Gly
                325                 330                 335
Ser Ser Gln His Ile Leu Ser Ser Leu Arg Phe Val Phe Cys Phe Pro
            340                 345                 350
His Gly Asp Leu Thr Glu Phe Gly Phe Leu Met Pro Glu Leu Cys Leu
        355                 360                 365
Val Leu Lys Val Arg His Ser Glu Asn Thr Leu Phe Ile Ile Ser Asp
    370                 375                 380
Ala Ala Asn Leu His Glu Phe His Ala Asp Leu Arg Ser Cys Phe Ala
385                 390                 395                 400
Pro Gln His Met Ala Met Leu Cys Ser Pro Ile Leu Tyr Gly Ser His
                405                 410                 415
Thr Ser Leu Gln Glu Phe Leu Arg Gln Leu Leu Thr Phe Tyr Lys Val
```

-continued

```
            420                 425                 430
Ala Gly Gly Cys Gln Glu Arg Ser Gln Gly Cys Phe Pro Val Tyr Leu
        435                 440                 445
Val Tyr Ser Asp Lys Arg Met Val Gln Thr Ala Ala Gly Asp Tyr Ser
    450                 455                 460
Gly Asn Ile Glu Trp Ala Ser Cys Thr Leu Cys Ser Ala Val Arg Arg
465                 470                 475                 480
Ser Cys Cys Ala Pro Ser Glu Ala Val Lys Ser Ala Ala Ile Pro Tyr
                485                 490                 495
Trp Leu Leu Leu Thr Pro Gln His Leu Asn Val Ile Lys Ala Asp Phe
            500                 505                 510
Asn Pro Met Pro Asn Arg Gly Thr His Asn Cys Arg Asn Arg Asn Ser
        515                 520                 525
Phe Lys Leu Ser Arg Val Pro Leu Ser Thr Val Leu Leu Asp Pro Thr
    530                 535                 540
Arg Ser Cys Thr Gln Pro Arg Gly Ala Phe Ala Asp Gly His Val Leu
545                 550                 555                 560
Glu Leu Leu Val Gly Tyr Arg Phe Val Thr Ala Ile Phe Val Leu Pro
                565                 570                 575
His Glu Lys Phe His Phe Leu Arg Val Tyr Asn Gln Leu Arg Ala Ser
            580                 585                 590
Leu Gln Asp Leu Lys Thr Val Val Ile Ala Lys Thr Pro Gly Thr Gly
        595                 600                 605
Gly Ser Pro Gln Gly Ser Phe Ala Asp Gly Gln Pro Ala Glu Arg Arg
    610                 615                 620
Ala Ser Asn Asp Gln Arg Pro Gln Glu Val Pro Ala Glu Ala Leu Ala
625                 630                 635                 640
Pro Ala Pro Val Glu Val Pro Ala Pro
                645                 650

<210> SEQ ID NO 7
<211> LENGTH: 390
<212> TYPE: PRT
<213> ORGANISM: Homo sapiens

<400> SEQUENCE: 7

Glu Glu Glu Glu Glu Glu Asp Glu Glu Ala Glu Glu Glu Arg Leu Ala
1               5                   10                  15
Leu Glu Trp Ala Leu Gly Ala Asp Glu Asp Phe Leu Leu Glu His Ile
                20                  25                  30
Arg Ile Leu Lys Val Leu Trp Cys Phe Leu Ile His Val Gln Gly Ser
            35                  40                  45
Ile Arg Gln Phe Ala Ala Cys Leu Val Leu Thr Asp Phe Gly Ile Ala
        50                  55                  60
Val Phe Glu Ile Pro His Gln Glu Ser Arg Gly Ser Ser Gln His Ile
65                  70                  75                  80
Leu Ser Ser Leu Arg Phe Val Phe Cys Phe Pro His Gly Asp Leu Thr
                85                  90                  95
Glu Phe Gly Phe Leu Met Pro Glu Leu Cys Leu Val Leu Lys Val Arg
            100                 105                 110
His Ser Glu Asn Thr Leu Phe Ile Ile Ser Asp Ala Ala Asn Leu His
        115                 120                 125
Glu Phe His Ala Asp Leu Arg Ser Cys Phe Ala Pro Gln His Met Ala
    130                 135                 140
Met Leu Cys Ser Pro Ile Leu Tyr Gly Ser His Thr Ser Leu Gln Glu
145                 150                 155                 160
Phe Leu Arg Gln Leu Leu Thr Phe Tyr Lys Val Ala Gly Gly Cys Gln
                165                 170                 175
Glu Arg Ser Gln Gly Cys Phe Pro Val Tyr Leu Val Tyr Ser Asp Lys
            180                 185                 190
Arg Met Val Gln Thr Ala Ala Gly Asp Tyr Ser Gly Asn Ile Glu Trp
        195                 200                 205
Ala Ser Cys Thr Leu Cys Ser Ala Val Arg Arg Ser Cys Cys Ala Pro
    210                 215                 220
Ser Glu Ala Val Lys Ser Ala Ala Ile Pro Tyr Trp Leu Leu Leu Thr
225                 230                 235                 240
Pro Gln His Leu Asn Val Ile Lys Ala Asp Phe Asn Pro Met Pro Asn
                245                 250                 255
Arg Gly Thr His Asn Cys Arg Asn Arg Asn Ser Phe Lys Leu Ser Arg
            260                 265                 270
Val Pro Leu Ser Thr Val Leu Leu Asp Pro Thr Arg Ser Cys Thr Gln
        275                 280                 285
Pro Arg Gly Ala Phe Ala Asp Gly His Val Leu Glu Leu Leu Val Gly
    290                 295                 300
Tyr Arg Phe Val Thr Ala Ile Phe Val Leu Pro His Glu Lys Phe His
305                 310                 315                 320
Phe Leu Arg Val Tyr Asn Gln Leu Arg Ala Ser Leu Gln Asp Leu Lys
```

```
                        325                 330                 335
        Thr Val Val Ile Ala Lys Thr Pro Gly Thr Gly Gly Ser Pro Gln Gly
                    340                 345                 350
        Ser Phe Ala Asp Gly Gln Pro Ala Glu Arg Arg Ala Ser Asn Asp Gln
                355                 360                 365
        Arg Pro Gln Glu Val Pro Ala Glu Ala Leu Ala Pro Ala Pro Val Glu
            370                 375                 380
        Val Pro Ala Pro Ala Pro
        385                 390
```

```
<210> SEQ ID NO 8
<211> LENGTH: 20
<212> TYPE: DNA
<213> ORGANISM: Homo sapiens

<400> SEQUENCE: 8
cttgaggatg cggatgtgct                                           20

<210> SEQ ID NO 9
<211> LENGTH: 18
<212> TYPE: DNA
<213> ORGANISM: Homo sapiens

<400> SEQUENCE: 9
ccatggggtg agtgtcct                                             18

<210> SEQ ID NO 10
<211> LENGTH: 18
<212> TYPE: DNA
<213> ORGANISM: Homo sapiens

<400> SEQUENCE: 10
aggacactca ccccatgg                                             18

<210> SEQ ID NO 11
<211> LENGTH: 20
<212> TYPE: DNA
<213> ORGANISM: Homo sapiens

<400> SEQUENCE: 11
gtatgggaca ggggcagaaa                                           20

<210> SEQ ID NO 12
<211> LENGTH: 20
<212> TYPE: DNA
<213> ORGANISM: Homo sapiens

<400> SEQUENCE: 12
tttctaaaga ccattgggag                                           20

<210> SEQ ID NO 13
<211> LENGTH: 20
<212> TYPE: DNA
<213> ORGANISM: Homo sapiens

<400> SEQUENCE: 13
ccattttaaa gtagcggttc                                           20

<210> SEQ ID NO 14
<211> LENGTH: 20
<212> TYPE: DNA
<213> ORGANISM: Homo sapiens

<400> SEQUENCE: 14
aggagagaaa ggtgagccaa                                           20
```

```
<210> SEQ ID NO 15
<211> LENGTH: 20
<212> TYPE: DNA
<213> ORGANISM: Homo sapiens

<400> SEQUENCE: 15
gtagatcctg aggttgacca                                              20

<210> SEQ ID NO 16
<211> LENGTH: 20
<212> TYPE: DNA
<213> ORGANISM: Homo sapiens

<400> SEQUENCE: 16
tgtgagcatt tctggccttc                                              20

<210> SEQ ID NO 17
<211> LENGTH: 20
<212> TYPE: DNA
<213> ORGANISM: Homo sapiens

<400> SEQUENCE: 17
tgaagacgcc agagaagcag                                              20

<210> SEQ ID NO 18
<211> LENGTH: 20
<212> TYPE: DNA
<213> ORGANISM: Homo sapiens

<400> SEQUENCE: 18
gcctcacaag tgtcagacct                                              20

<210> SEQ ID NO 19
<211> LENGTH: 18
<212> TYPE: DNA
<213> ORGANISM: Homo sapiens

<400> SEQUENCE: 19
agaagggtgg tgaagact                                                18

<210> SEQ ID NO 20
<211> LENGTH: 20
<212> TYPE: DNA
<213> ORGANISM: Homo sapiens

<400> SEQUENCE: 20
cttggttaga gaggatgggc                                              20

<210> SEQ ID NO 21
<211> LENGTH: 20
<212> TYPE: DNA
<213> ORGANISM: Homo sapiens

<400> SEQUENCE: 21
gcccatcctc tctaaccaag                                              20
```

DNA ENCODING A HUMAN IMIDAZOLINE RECEPTOR AND LIGAND BINDING ASSAY EMPLOYING SAME

REFERENCE TO RELATED APPLICATION

The present application is related to provisional application Ser. No. 60/12,600, filed Mar. 1, 1996.

BACKGROUND OF THE INVENTION

1. Field of the Invention

The present invention is directed to a cDNA clone encoding a human imidazoline receptive protein, designated as an imidazoline receptor subtype-1 (abbreviated $IR_1$), and fragments thereof. Also, the invention relates to an $IR_1$ polypeptide encoded by the cDNA, as well as fragments containing the receptor binding site(s). The invention also relates to methods for producing such a cDNA clone, methods for expressing the $IR_1$ protein, and uses thereof.

2. Description of Related Art

It is believed that brainstem imidazoline receptors possess binding site(s) for therapeutically relevant imidazoline compounds, such as clonidine and idazoxan. These drugs represent the first generation of ligands for the binding site(s) of imidazoline receptors. However, clonidine and idazoxan are also known to possess high affinity for $\alpha_2$-adrenergic receptors. Second generation ligands, such as moxonidine, possess somewhat improved selectivity for $IR_1$ over $\alpha_2$-adrenergic receptors, but more selective compounds for $IR_1$ are needed.

An imidazoline receptor clone is of particular interest because of its potential utility in identifying novel pharmaceutical agents having greater potency and/or more selectivity than currently available ligands have for imidazoline receptors. Recent technological advances permit pharmaceutical companies to use combinatorial chemistry techniques to rapidly screen a cloned receptor for ligands (drugs) binding thereto. Thus, a cloned imidazoline receptor would be of significant value to a drug discovery program.

Until now, the molecular nature of imidazoline receptors remains unknown. For instance, no amino acid sequence data for $IR_1$, e.g., by N-terminal sequencing, has been reported. Three different techniques have been described in the literature by three different laboratories to visualize imidazoline-selective binding proteins (imidazoline receptor candidates) using gel electrophoresis. Some important consistencies have emerged from these results despite the diversity of the techniques employed. On the other hand, multiple protein bands have been identified, which suggests heterogeneity amongst imidazoline receptors. These reports are discussed below.

Some of the abbreviations used hereinbelow, have the following meanings:

| | |
|---|---|
| $\alpha_2AR$ | Alpha-2 adrenoceptor |
| BAC | Bovine adrenal chromaffin |
| ECL | Enhanced chemiluminescence (protein detection procedure) |
| EST | Expressed Sequence Tag |
| I-site | Any imidazoline-receptive binding site (e.g., encoded on $IR_1$) |
| $IR_1$ | Imidazoline receptor subtype |
| IR-Ab | Imidazoline receptor antibody |
| $I_2$Site | Imidazoline binding subtype |
| kDa | Kilodaltons (molecular size) |
| MAO | monoamine oxidase |
| MW | molecular weight |
| NRL | European abbreviation for RVLM (see below) |
| PC-12 | Phaeochromocytoma-12 cells |
| $^{125}$PIC | [$^{125}$I]p-iodochlodine |
| PKC | Protein Kinase C |
| RVLM | Rostral Ventrolateral Medulla in brainstem |
| SDS | sodium dodecyl sulfate gel electrophoresis. |

Reis et al. [Wang et al., *Mol. Pharm.*, 42: 792-801 (1992); Wang et al., *Mol. Pharm.*, 43: 509-515 (1993)] were the first to demonstrate partial purification of an imidazoline-selective binding protein and to characterize it as having MW=70 kDa. This was accomplished using bovine cells (BAC), which lack an $\alpha_2AR$ [Powis & Baker, *Mol. Pharm.*, 29:134-141 (1986)]. The 70 kDa imidazoline-selective protein in those studies had high affinities for both idazoxan and p-aminoclonidine affinity chromatography columns. To date, no one has reported the complete purification of this imidazoline receptor protein. Likewise, no amino acid sequences have been reported for $IR_1$.

The partially purified 70 kDa protein was used by Reis and co-workers to raise "I-site binding antiserum", designated herein as Reis antiserum. The term "I-site" refers to the imidazoline binding site, presumably defined within the imidazoline receptor protein. Reis antiserum was prepared by injecting the purified protein into rabbits [Wang et al, 1992]. The first immunization was done subcutaneously with the protein antigen (10 μg) emulsified in an equal volume of complete Freund's adjuvant, and the next three booster shots were given at 15-day intervals with incomplete Freund's adjuvant. The polyclonal antiserum has been mostly characterized by immunoblotting, but radioimmunoassays (RIA) and/or conjugated assay procedures, i.e., ELISA assays, are also conceivable [see "Radioimmunoassay of Gut Regulatory Peptides: Methods in Laboratory Medicine," Vol. 2, chapters 1 and 2, Praeger Scientific Press, 1982].

The present inventors and others [Escriba et al., *Neurosci. Lett.* 178: 81-84 (1994)] have characterized the Reis antiserum in several respects. For instance, the present inventors have discovered that human platelet immunoreactivity with Reis antiserum is mainly confined to a single protein band of MW=33 kDa, although a trace band at 85 kDa was also observed. This 33 kDa band was enriched in plasma membrane fractions as expected for an imidazoline receptor. Furthermore, the intensity of this band was found to be positively correlated with non-adrenergic $^{125}$PIC Bmax values at platelet $IR_1$ sites in samples from the same subjects, with an almost one-to-one slope factor. In addition, the nonadrenergic $^{125}$PIC binding sites on platelets were discovered by the present inventors to have the same rank order of affinities as $IR_1$ binding sites in brainstem [Piletz and Sletten, *J.Pharm. & Exper. Therap.*, 267: 1493-1502 (1993)]. The platelet 33 kDa band may also be a product of a larger protein, since in human megakaryoblastoma cells, which are capable of forming platelets in tissue cultures, an 85 kDa immunoreactive band was found to predominate.

Immunoreactivity with Reis antiserum does not appear to be directed against human $\alpha_2AR$ and/or MAO A/B. This is significant because $\alpha_2AR$ and MAO A/B have previously been cloned and also bind to imidazolines. The present inventors have obtained selective antibodies and recombinant preparations for $\alpha_2AR$ and MAO A/B, and these proteins do not correspond to the 33, 70, or 85 kDa putative IR$_1$ bands. Thus, there is substantial evidence that, at least in human platelets, the Reis antiserum is IR$_1$ selective.

Another antiserum was raised by Drs. Dontenwill and Bousquet in France [Greney et al., *Europ. J. Pharmacol.*, 265: R1-R2 (1994); Greney et al., *Neurochem. Int.*, 25: 183-191 (1994); Bennai et al., *Annals NY Acad. Sci.*, 763: 140-148 (1995)] against polyclonal antibodies for idazoxan (designated Dontenwill antiserum). This anti-idiotypic antiserum inhibits $^3$H-clonidine but not $^3$H-rauwolscine ($\alpha_2$-selective) binding sites in the brainstem, suggesting it interacts with IR$_1$ [Bennai et al., 1995]. As shown in FIG. 1, human RVLM (same as NRL) membrane fractions displayed bands of 41 and 44 kDa, as detected by the present inventors using this anti-idiotypic antiserum.

The present inventors have found that the bands of MW=41 and 44 kDa detected by Dontenwill antiserum may be derived from an 85 kDa precursor protein, similar to that occurring in platelet precursor cells. An 85 kDa immunoreactive protein is obtained in fresh rat brain membranes only when a cocktail of 11 protease inhibitors is used. Also, as shown in FIG. 1, it is found that Reis antiserum detects the 41 and 44 kDa bands in human brain when fewer protease inhibitors are used. Additionally, the Dontenwill antiserum weakly detects the platelet 33 kDa band. Thus, the present inventors have hypothesized that the 41 and 44 kDa immunoreactive proteins may be alternative breakdown products of an 85 kDa protein, as opposed to the platelet 33 kDa breakdown product.

In summary, the main conclusion from the above results is that, despite vastly different origins, the Reis and Dontenwill antisera both detect identical bands in human platelets, RVLM, and hippocampus.

Using yet another technique, a photoaffinity imidazoline ligand, $^{125}$AZIPI, has also been developed to preferentially label I$_2$-imidazoline binding sites [Lanier et al., *J. Biol. Chem.*, 268: 16047-16051 (1993)]. The $^{125}$AZIPI photoaffinity ligand was used to visualize 55 kDa and 61 kDa binding proteins from rat liver and brain. It is believed that the 61 kDa protein is probably MAO, in agreement with other findings [Tesson et al., *J.Biol.Chem.*, 270: 9856-9861 (1995)] showing that MAO proteins bind certain imidazoline compounds. The different molecular weights between these bands and those studied by the present inventors is one of many pieces of evidence that distinguishes IR$_1$ from I$_2$ sites.

To the inventors' knowledge and as described herein, we are first to clone a cDNA encoding a protein with the immunological and ligand binding properties expected of an IRK. We are first to identify the nucleotide sequence of a DNA molecule encoding an imidazoline receptor, and first to determine the amino acid sequence of an imidazoline receptor. The polypeptides described herein are clearly distinct from $\alpha_2$AR or MAO A/B proteins.

SUMMARY OF THE INVENTION

The present invention is for an isolated polypeptide that is receptive to (binds to) an imidazoline compound. Exemplary imidazoline compounds in this context are p-iodoclonidine and moxonidine. Typically, such a polypeptide immunoreacts with Reis antiserum and/or Dontenwill antiserum.

In one aspect of the invention, a polypeptide includes a 651 amino acid sequence as shown in SEQ ID No. 6. Other imidazoline receptive proteins homologous to this polypeptide are also contemplated. Such a protein generally has a molecular weight of about 60 to 80 kDa. More particularly, it can have a molecular weight of about 70 kDa.

In another aspect of the invention, a polypeptide includes a 390 amino acid sequence as shown in SEQ ID No. 7. Such a polypeptide generally has a molecular weight of about 35 to 45 kDa. More particularly, it can have a molecular weight of about 37 kDa.

A DNA molecule encoding an aforementioned imidazoline-receptive polypeptide is also contemplated. Such a DNA molecule, e.g., a cDNA derived from mRNA, can contain a nucleotide sequence encoding the amino acid sequence shown in SEQ ID No. 6. Thus, a DNA molecule containing the 1678 base pair (b.p.) (1677/3=559) nucleotide sequence shown in SEQ ID No. 2 is contemplated. In another embodiment, a DNA molecule includes the longer nucleotide sequence shown in SEQ ID No. 3.

In another embodiment of the invention, a DNA molecule contains a nucleic acid sequence encoding the amino acid sequence shown in SEQ ID No. 7. Such a DNA molecule can include the 895 base pair nucleic acid sequence shown in SEQ ID No. 4. In another aspect, it can include the 1171 base pair nucleic acid sequence shown in SEQ ID No. 5.

RNA molecules complementary to an instant DNA molecule, e.g., an mRNA molecule (sense) or a complementary cRNA molecule (antisense), is a further aspect of the invention.

A further aspect of the invention is for a recombinant vector, as well as a host cell transfected with the recombinant vector, wherein the recombinant vector contains at least one of the nucleotide sequences shown in SEQ ID Nos. 2-5, or a nucleotide sequence homologous thereto.

A method of producing an imidazoline receptor protein is another aspect of the invention. Such a method entails transfecting a host cell with an aforementioned vector, and culturing the transfected host cell in a culture medium to generate the imidazoline receptor.

A significant further aspect of the invention is a method of screening for a ligand that binds to an imidazoline receptor. Such a method can comprise culturing an above-mentioned host cell in a culture medium to express imidazoline receptor proteins, followed by contacting the proteins with a labelled ligand for the imidazoline receptor under conditions effective to bind the labelled ligand thereto. The imidazoline receptor proteins can then be contacted with a candidate ligand, and any displacement of the labelled ligand from the proteins can be detected. Displacement of labelled-ligand signifies that the candidate ligand is a ligand for the imidazoline receptor. These steps can be performed on intact host cells, or on proteins isolated from the cell membranes of the host cells.

The invention will now be described in more detail with reference to specific examples.

BRIEF DESCRIPTION OF THE DRAWINGS

FIG. 4 depicts a competitive binding assay between $^{125}$I-labelled p-iodoclonidine (PIC) and various ligands for the imidazoline receptor on membranes expressed in COS cells transfected with the $IR_1$ cDNA clone, as discussed in Example 3.

DETAILED DESCRIPTION OF THE INVENTION

Figures 1A, 1B:
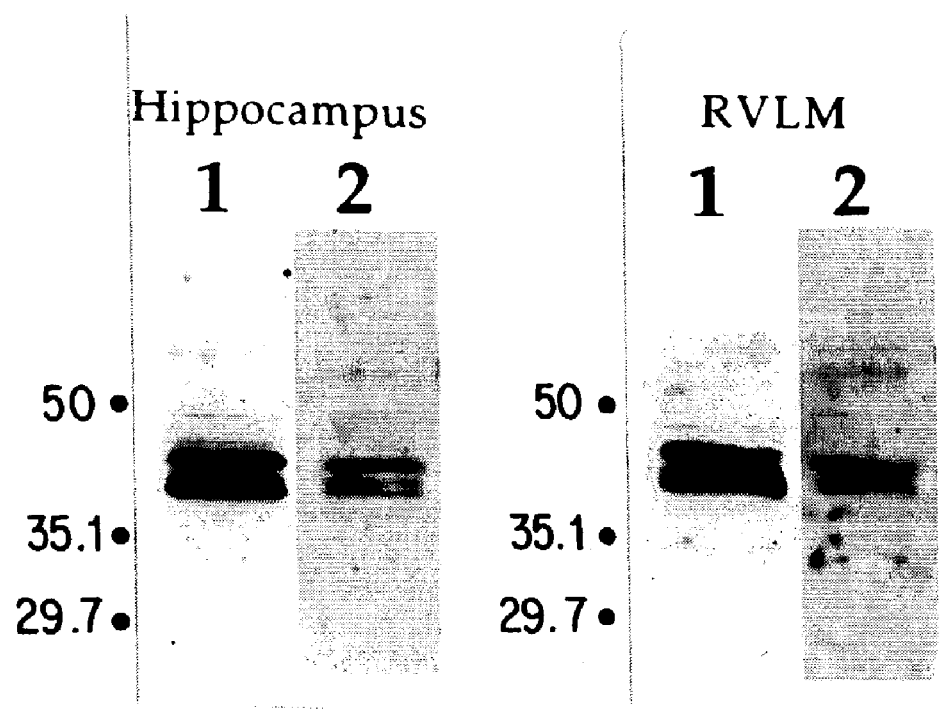
FIG. 1 depicts a comparison of Reis antiserum (lane 1, 1:2000 dilution) and Dontenwill antiserum (lane 2, 1:5000 dilution) immunoreactivities for human NRL (same as RVLM) and hippocampus, as discussed in Example 1.

The present invention concerns multiple aspects of the imidazoline receptor protein, and DNA molecule encoding the same, which have now been discovered.

First, a polypeptide-having imidazoline binding activity has been identified, as well as fragments thereof which contain the putative active site for binding, as discussed hereinafter. Although a polypeptide described herein has a binding affinity for an imidazoline compound, it may also have an enzymatic activity, such as do catalytic antibodies and ribozymes.

Exemplary polypeptides are those containing either of the amino acid sequences shown in SEQ ID Nos. 6 or 7 (with the full length (651 residue) amino acid sequence given in SEQ ID No. 6). Functionally equivalent polypeptides are also contemplated, such as those having a high degree of homology with an aforementioned polypeptide, particularly when they contain the Glu-Asp-rich region described hereinafter which is believed to define an active imidazoline binding site.

A polypeptide of the invention can be formed by direct chemical synthesis on a solid support using the carbodiimide method [R. Merrifield, *JACS*, 85: 2143 (1963)]. Alternatively, and preferably, an instant polypeptide can be produced by a recombinant DNA technique as described herein and elsewhere [e.g., U.S. Pat. No. 4,740,470 (issued to Cohen and Boyer), the disclosure of which is incorporated herein by reference], followed by culturing transformants in a nutrient broth.

Second, a DNA molecule of the present invention encodes an aforementioned polypeptide. Thus, any of the degenerate set of codons encoding an instant polypeptide is contemplated. A particularly preferred coding sequence is the 1678 base pair sequence set forth in SEQ ID No. 2, which has now been discovered to be the native nucleotide sequence that encodes the 70 kDa human $IR_1$ protein of the invention. In another embodiment, a DNA molecule includes the 3318 base pair nucleotide sequence shown in SEQ ID No. 3. This latter sequence includes the nucleotide sequence of SEQ ID No. 2, as well as additional nonplasmid, noncoding cDNA at the 5' and 3' ends of the protein-coding sequence.

In another embodiment of the invention, a DNA molecule contains a nucleic acid sequence encoding the amino acid sequence (290 residues) shown in SEQ ID No. 7. This amino acid sequence corresponds to that derived from direct sequencing of the 5A-1 clone described hereinafter, and represents a C-terminal fragment of the native protein. Preferably, a DNA molecule includes the native 895 base pair nucleic acid sequence shown in SEQ ID No. 4, which was derived from the 5A-1 clone. A DNA molecule can also include the 1171 base pair nucleic acid sequence shown in SEQ ID No. 5,which includes non-plasmid cDNA at its 3' (noncoding) end.

A DNA molecule of the present invention can be synthesized according to the phosphotriester method [Matteucci et al., *JACS*, 103: 3185 (1988)]. This method is particularly suitable when it is desired to effect site-directed mutagenesis of an instant DNA sequence, whereby a desired nucleotide substitution can be readily made. Another method for making an instant DNA molecule is by simply growing cells transformed with plasmids containing the DNA sequence, lysing the cells, and isolating the plasmid DNA molecules. Preferably, an isolated DNA molecule of the invention is made by employing the polymerase chain reaction (PCR) [e.g., U.S. Pat. No. 4,683,202 (issued to Mullis)] using synthetic primers that anneal to the desired DNA sequence, whereby DNA molecules containing the desired nucleotide sequence are amplified. Also, a combination of the above methods can be employed, such as one in which synthetic DNA is ligated to cDNA to produce a quasi-synthetic gene [e.g., U.S. Pat. No. 4,601,980 (issued to Goeddel et al.)]

A further aspect of the invention is for a vector, e.g., a plasmid, that contains at least one of the nucleotide sequences shown in SEQ ID Nos. 2-5. Whenever the reading frame of the vector is appropriately selected, the vector encodes an $IR_1$ polypeptide of the invention. Hence, a fragment of the native $IR_1$ protein is contemplated, as well as fusion proteins that incorporate an amino acid sequence as described herein. Also, a vector containing a nucleotide sequence having a high degree of homology with any of SEQ ID Nos. 2-5 is contemplated within the invention, particularly when it encodes a protein having imidazoline binding activity.

A recombinant vector of the invention can be formed by ligating an afore-mentioned DNA molecule to a preselected expression plasmid, e.g., with T4 DNA ligase. Preferably, the plasmid and DNA molecule are provided with cohesive (overlapping) termini, with the plasmid and DNA molecule operatively linked (i.e., in the correct reading frame).

Another aspect of the invention is a host cell transfected with a vector of the invention. Relatedly, a protein expressed by a host cell transfected with such a vector is contemplated, which protein may be bound to the cell membrane. Such a protein can be identical with an aforementioned polypeptide, or it can be a fragment thereof, such as when the polypeptide has been partially digested by a protease in the cell. Also, the expressed protein can differ from an aforementioned polypeptide, as whenever it has been subjected to one or more post-translational modifications. For the protein to be useful within the context of the present invention, it still should retain imidazoline binding activity.

A method of producing an imidazoline receptor protein is another aspect of the invention, which entails transfecting a host cell with an aforementioned vector, and culturing the transfected host cell in a culture medium to generate the imidazoline receptor. The receptor molecule can undergo any post-translational modification, including proteolytic decomposition, whereby its structure is altered from the basic amino acid residue sequence encoded by the vector. A suitable transfection method is electroporation, and the like.

With respect to transfecting a host cell with a vector of the invention, it is contemplated that a vector encoding an instant polypeptide can be transfected directly in animals. For instance, embryonic stem cells can be transfected, and the cells can be manipulated in embryos to produce transgenic animals. Methods for performing such an operation have been previously described [Bond et al., *Nature*, 374: 272-276 (1995)]. These methods for expressing an instant cDNA molecule in either tissue culture cells or in animals can be especially useful for drug discovery.

Possibly the most significant aspect of the present invention is in its potential for affording a method of screening for a ligand (drug) that binds to an imidazoline receptor. Such a method comprises culturing an above-mentioned host cell in a culture medium to express an instant imidazoline receptive polypeptide, then contacting the polypeptides with a labelled ligand, e.g., radiolabelled p-iodoclonidine, for the imidazoline receptor under conditions effective to bind the labelled ligand thereto. The polypeptides are further contacted with a candidate ligand, and any displacement of the labelled ligand from the polypeptides is detected. Displacement signifies that the candidate ligand actually binds to the imidazoline receptor. These steps can be performed on intact host cells, or on proteins isolated from the cell membranes of the host cells.

Typically, a suitable drug screening protocol involves preparing cells (or possibly tissues from transgenic animals) that express an instant imidazoline receptive polypeptide. This process is currently referred to as combinatorial chemistry. In this process, categories of chemical structure are systematically screened for binding affinity or activation of the receptor molecule encoded by the transfected cDNA. With respect to the imidazoline receptor, a number of commercially available radioligands, e.g., $^{125}$PIC, can be used for competitive drug binding affinity screening.

An alternative approach is to screen for drugs that elicit or block a second messenger effect known to be coupled to activation of the imidazoline receptor, e.g., moxonidine-stimulated arachidonic acid release. Even with a weak binding affinity or activation by one category of chemicals, systematic variations of that chemical structure can be studied and a preferred compound (drug) can be deduced as being a good pharmaceutical candidate. Identification of this compound would lead to animal testing and upwards to human trials, however, the initial rationale for drug discovery is vastly improved with an instant cloned imidazoline receptor.

Along these lines, a drug screening method is contemplated in which a host cell of the invention is cultured in a culture medium to express an instant imidazoline receptive polypeptide. Intact cells are then exposed to an identified agent (agonist, inverse agonist, or antagonist) under conditions effective to elicit a second messenger or other detectable response upon interacting with the receptor molecule. The imidazoline receptive polypeptides are then contacted with one or more candidate chemical compounds (drugs), and any modification in a second messenger response is detected. Compounds that mimic an identified agonist would be agonist candidates, and those producing the opposite response would be inverse agonist candidates. Those compounds that block the effects of a known agonist would be antagonist candidates for an in vivo imidazoline receptor. For meaningful results, the contacting step with a candidate compound is preferably conducted at a plurality of candidate compound concentrations.

A method of probing for a gene encoding an imidazoline receptor or homologous protein is further contemplated. Such a method comprises providing a DNA molecule identical or complementary to an above-described cDNA molecule, contacting the DNA molecule with genetic material suspected of containing a gene encoding an imidazoline receptor, or homologous protein, under stringent hybridization conditions (e.g., a high stringency wash condition is 0.1×SSC, 0.5% SDS at 65° C.), and identifying any portion of the genetic material that hybridizes to the DNA molecule.

Still further, a method of selectively producing antibodies, e.g., monoclonal antibodies, immunoreactive with an instant imidazoline-receptive protein comprises injecting a mammal with an aforementioned polypeptide, and isolating the antibodies produced by the mammal. This aspect is discussed in more detail in an example presented hereinafter.

The present inventors began their search for a human imidazoline receptor cDNA by screening a λgt11 phage human hippocampus cDNA expression library. Their preliminary research had indicated that both of the known antisera (Reis and Dontenwill) that are directed against human imidazoline receptors were immunoreactive with identical bands in the human hippocampus. By contrast other brain regions either were commercially unavailable as cDNA expression libraries or yielded inconsistencies between the two antisera. Therefore, it was felt that a human hippocampal cDNA library held the best opportunity for obtaining a cDNA for an imidazoline receptor. Immunoexpression screening was chosen over other cloning strategies because of its sensitivity when coupled with the ECL detection system used by the present inventors, as discussed hereinbelow.

Once an initial clone (5A-1) was identified, a more full-length clone was obtainable after DNA sequence analysis. The binding affinities of the expressed protein after transfection in COS cells were determined by radioligand binding procedures developed in the inventors' laboratory [Piletz and Sletten, 1993, ibid]. A number of unique discoveries, i.e., brain immunoreactivity regionalization studies, and adapting ECL to these antisera, led to our identification of an imidazoline receptor cDNA described herein.

To identify an instant cDNA clone encoding an imidazoline receptor it was necessary to employ both of the known antibodies to imidazoline receptors. These antibodies were obtained by contacting Dr. D. Reis (Cornell University Medical Center, New York City), and Drs. M. Dontenwill and P. Bousquet (Laboratoire de Pharmacologie Cardiovasculaire et Renale, CNRS, Strasbourg, France). These antisera were obtained free of charge and without confidentiality or restrictions on their use. The former antiserum (Reis antiserum): was derived from a published imidazoline receptor protein [Wang et al., (1992, 1993), the disclosures of which are incorporated herein by reference]. The method for raising the latter antiserum (Dontenwill antiserum) has also been published [Bennai et al., (1995), the disclosure of which is incorporated herein by reference]. The latter antiserum was derived using an anti-idiotypic approach that identified the pharmacologically correct (clonidine and idazoxan selective) binding site structure.

EXAMPLE 1

Selectivity of the Antisera

The obtained Reis antiserum had been prepared against a purified imidazoline binding protein isolated from BAC cells, which protein runs in denaturing-SDS gels at 70 kDa [Wang et al., 1992, 1993]. The Dontenwill antiserum is anti-idiotypic, and thus is believed to detect the molecular configuration of an imidazoline binding site domain in any species.

Both of these antisera have been tested to ensure that they are in fact selective for a human imidazoline receptor. In particular, we found that both of these antisera detected identical bands in human platelets and hippocampus, and in brainstem RVLM (NRL) by Western blotting (see FIG. 1). In these studies, in order to increase sensitivity over previously published detection methods, an ECL (Enhanced Chemiluminescence) system was employed. The linearity of response of the ECL system was demonstrated with a standard curve. ECL detection was demonstrated to be very quantifiable and about ten times more sensitive than other methods previously used with these antisera. Western blots with antiserum dilutions of 1:3000 revealed immunoreactivity with as little as 1 ng of protein from a human hippocampal homogenate by dot blot analysis.

For the studies depicted in FIG. 1, human hippocampal homogenate (30 µg) and NRL membrane proteins (10 µg) were electrophoresed through a 12.5% polyacrylamide gel, electrotransfered to nitrocellulose and sequentially incubated with (1) the Reis antibody (1:2000 dilution) and (2) the Dontenwill antibody (1:5000 dilution). Immunoreactive bands were visualized with an Enhanced Chemiluminescence (ECL) detection kit (Amersham) using anti-rabbit Ig-HRP conjugated antibody at a dilution of 1:3000 and the ECL detection reagents. Following detection with the antibody, blots were stripped and reprocessed omitting the primary antibody to check for complete removal of this antibody. In panels A and B, lane 1 shows the immunoreactive bands observed with the Reis antibody and lane 2 shows the bands detected with the Dontenwill antibody. Protein molecular weight standards are indicated to the left of each panel (in kDa).

Despite the diverse origins of Reis and Dontenwill antisera, both of these antisera detected a 33 kDa band in human platelets. Although this band is of smaller size than that reported for other tissues [Wang et al., 1993; Escriba et al., 1994; Greney et al., 1994], the fact that both antisera detected it suggests an imidazoline binding peptide. The 33 kDa band was enriched in platelet plasma membrane fractions, as is known to be the case for $IR_1$ binding, but not $I_2$ binding [Piletz and Sletten, 1993]. The present investigators also found that human cortex imidazoline receptor—antibody immunoreactivity is enriched in a plasma membrane fraction (pelleted at 100,000×g), but not in a mitochondrial fraction (pelleted at 20,000×g), which suggests that the brain receptor also exists within plasma membranes.

A significant positive correlation was observed within samples from 15 healthy platelet donors between $IR_1$ Bmax values (but not $I_2$ or $\alpha_2AR$ Bmax values), with the $IR_1$ immunoreactivity on Western blots. This correlation exhibited a slope factor close to unity (results not shown). This correlation strongly suggested that an $IR_1$ binding protein could be revealed in an imidazoline receptor—antibody Western blotting assay. Furthermore, the Reis antiserum failed to detect authentic $\alpha_2AR$, MAO A or MAO B bands on gels, i.e., it was not immunoreactive with MAO at MW=61 kDa, or $\alpha_2AR$ at MW 64 kDa. Additionally, no immunoreactive bands were observed using preimmune antiserum. Thus, after extensively characterizing these antisera with human materials, it was concluded that these antisera are indeed selective for a human imidazoline receptor protein.

EXAMPLE 2

Cloning of the Imidazoline Receptor

Figures 2A, 2B:
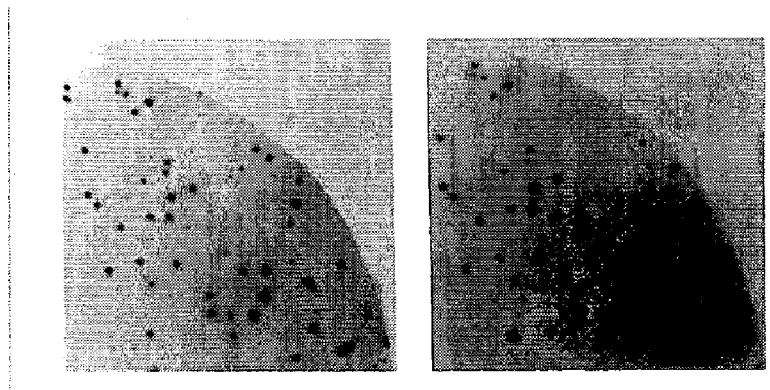
FIG. 2 depicts a comparison of Reis antiserum (1:15,000 dilution) and Dontenwill antiserum (1:20,000 dilution) immunoreactivities for plaques isolated from the human hippocampal cDNA library used in cloning as discussed in Example 2. The plaques contain the initial clone, designated herein as 5A-1, in a third stage of purification.

A commercially available human hippocampal cDNA λgtll expression library (Clontech Inc., Palo Alto, Calif.) was screened for immunoreactivity sequentially using both the anti-idiotypic Dontenwill antiserum and the Reis antiserum. Standard techniques to induce protein and transference to a nitrocellulose overlay were employed. [See, for instance, Sambrook et al., 1989, "Molecular Cloning: A Laboratory Manual," Cold Spring Harbor Laboratory Press]. After washing and blocking with 5% milk, the Dontenwill antiserum was added to the overlay at 1:20,000 dilution in Tris-buffered saline, 0.05% Tween20, and 5% milk. The Reis antiserum was employed similarly, but at 1:15,000 dilution. These high dilutions of primary antiserum were chosen to avoid false positives. Secondary antibody was added, and positive plaques were identified using ECL. Representative results are shown in FIG. 2.

Positive plaques were pulled and rescreened until tertiary screenings yielded only positive plaques. Four separate positive plaques were identified from more than 300,000 primary plaques in our library. Recombinant λgtll DNA purified from each of the four plaques was subsequently subcloned into E. coli pBluescript vector (Stratagene, La Jolla, Calif.). Sequencing of these four cDNA inserts in pBluescript demonstrated that they were identical, suggesting that only one cDNA had actually been identified four times. Thus, the screening had been verified as being highly reproducible and the frequency of occurrence was as expected for a single copy gene, i.e., one in 75,000 transcripts. As shown in FIG. 2, the protein produced by the first positive clone, designated 5A-1, tested positive with both the Reis antiserum and the Dontenwill antiserum. Tertiary-screened plaques of 5A-1 were all immuno-positive with either of the two known anti-imidazoline receptor antisera, but not with either preimmune antisera. These results suggested that clone 5A-1 encoded a fusion peptide similar to or identical with one of the predominant bands detected in human Western blots by both the Dontenwill and Reis antisera.

Sequencing of the four clones was performed by ACGT Company (Chicago, Ill.) after subcloning them into pbluescript vector SK (Stratagene). Both manual and automatic sequencing strategies were employed which are outlined as follows:

Manual Sequencing

1. DNA sequencing was performed using T7 DNA polymerase and the dideoxy nucleotide termination reaction.
2. The primer walking method [Sambrook et al., ibid.] was used in both directions.
3. ($^{35}$S)dATP was used for labelling.
4. The reactions were analyzed on 6% polyacrylamide wedge or non-wedge gels containing 8 M urea, with samples being loaded in the order of A C G T.
5. DNA sequences were analyzed by MacVector Version 5.0. and by various Internet-available programs, i.e., the BLAST program.

Automatic Sequencing

1. DNA sequencing was performed by the fluorescent dye terminator labelling method using AmpliTaq DNA polymerase (Applied Biosystems Inc. Prizm DNA Sequencing Kit, Perkin-Elmer Corp., Foster City, Calif.).
2. The primer walking method was used. The primers actually used were a subset of those shown in SEQ ID Nos. 8-21.
3. Sequencing reactions were analyzed on an Applied Biosystems, Inc. (Foster City, Calif.) sequence analyzer.

These results demonstrated that the initial clone (5A-1) contained a 1171 base pair insert (see SEQ ID No. 5). Only one extended open reading frame for translation into protein was found possible. Consequently, it was determined that the 5A-1 cDNA derived from mRNA encoding 298 amino acids, which ended at a carboxy terminal cysteine (the TAG termination codon was at base pairs 895-898 in the 5A-1 sequence). The 895 base pair nucleotide sequence of the coding region of the 5A-1 clone is shown in SEQ ID No. 4. Thus, clone 5A-1 defined approximately 53% of the 70,000 MW protein predicted.

Using programs and databases available on the Internet (retrieved from NCBI Blast E-mail Server address blast@ncbi.nlm.nih.gov), it was determined that the 5A-1 clone encodes a unique molecule. The BLASTP program

[1.4.8MP, 20 Jun. 1995 (build Nov. 13, 1995)] was used to compare all of the possible frames of amino acid sequences encoded by 5A-1 versus all known amino acid sequences available within multiple international databases [Altschul et al., *J. Mol. Biol.*, 215: 403-410 (1990)]. Only one protein, from *Micrococcus luteus*, possessed a marginally significant homology (p=0.04)(41%) over a short stretch of 75 of the 298 amino acids encoded by 5A-1. Otherwise, there were no significant amino acid homologies (i.e., with p≦0.05) for any known proteins. Therefore, the protein encoded by 5A-1 is not significantly related to MAO A or B, $\alpha_2$AR, or any other known eukaryotic protein in the literature.

In contrast to the amino acid search on BLASTP, two partially homologous cDNA sequences covering 155 and 250 b.p. of the 5A-1 clone were discovered to exist using BLASTN (reached from the same Internet server). BLASTN is a program used to compare known DNA sequences from international databases, regardless of whether they encode a polypeptide. Neither of the two cDNA sequences having high homology to 5A-1 have been reported anywhere else except on the Internet. Both were derived as Expressed Sequence Tags (ESTs) in random attempts to sequence the human cDNA repertoire [as described in Adams et al., *Science*, 252: 1651-1656 (1991)]. As far as can be determined, the discoverers of these ESTs lack any knowledge of the protein they encode. One cDNA, designated HSA09H122, contained 250 b.p. with 7 unknown/incorrect base pairs (97% homology) versus 5A-1 over the same region. HSA09H122 was generated in France (Genethon, B.P. 60, 91002 Evry Cedex France) from a human lymphoblast cDNA library. The other EST, designated EST04033, contained 155 b.p. with 12 unknown/incorrect base pairs (92% homology) versus 5A-1 over the same region. EST04033 was generated at the Institute for Genomic Research (Gaithersburg, Md.) from a human fetal brain cDNA clone (HFBDP28). Thus, both of these ESTs are short DNA sequences and contain a number of errors (typical of single-stranded sequencing procedures as used when randomly screening ESTs).

Based on the BLASTN search, the owner of HSA09H122 was contacted in an effort to obtain that clone. The current owner of the clone appears to be Dr. Charles Auffret (Paul Brousse Hospital, Genetique, B.P. 8, 94801 Villejuif Cedex, France). Dr. Auffret indicated by telephone that his clone came from a lot of clones believed to be contaminated with yeast DNA, and he did not choose to release it. Contamination with yeast DNA was later confirmed to have been reported within an Internet database. Thus, HSA09H122 was not deemed reliable.

The other partial clone (EST04033) was purchased from the American Type Culture Collection (ATCC catalog no. 82815) (Rockville, Md.). A telephone call to the Institute for Genomic Research revealed that it had been deposited at ATCC recently. As far as can be determined, the present inventors were the first to sequence the full length insert of EST04033. The full length of EST04033 sequenced was 3385 base pair (SEQ ID No. 1), with a 3318 base pair nonplasmid insert (see SEQ ID No. 3). Within this sequence of EST04033 the remaining 783 base pairs of the coding sequence predicted for a 70 kDa imidazoline receptor were obtained (i.e., 783 b.p. in EST04033+894 b.p. of 5A-1=1677 total coding nucleotides). The entire 1678 base pair coding region for the 70 kDa protein is shown in SEQ ID No. 2. It is important to note that all of the 155 b.p. reported for EST04033 on the Internet were located at the 3' end outside of the coding region. Thus, the present inventors are first to sequence any of the coding region of an instant imidazoline receptor.

The nucleotide sequence of EST04033 was determined in the same manner as described previously for the 5A-1 clone. The nucleotide sequence of the entire clone is shown in SEQ ID No: 1. In this sequence, an identical overlap was observed for the sequence obtained previously for the 5A-1 clone and the sequence obtained for EST04033. The 5A-1 overlap began at EST04033 b.p. 2,181 and continued to the end of the molecule (b.p. 3,350).

The nucleotide sequence identified contains an open reading frame for a 70 kDa protein, which is the same size as the protein originally isolated as the putative bovine imidazoline receptor purified by Reis and coworkers [Wang et al., 1992] from which the Reis antiserum was subsequently derived [Wang et al., 1993].

Of further interest is a unique glutamic- and aspartic acid-rich coding region within the clone. This region of the $IR_1$ cDNA encodes a highly unique span of 59 amino acids, 36 of which are Glu or Asp residues (61%). This region is largely contained within clone 5A-1 and is just upstream from apparent transmembrane loops and an ultimate polar carboxy terminus tail. Since the Dontenwill antiserum is specifically directed against an idazoxan/clonidine binding site, and its immunoreactivity is directed against the clone 5A-1/□gtll fusion protein, this suggests that clone 5A-1 encodes the binding site of the imidazoline receptor. The identification of this unique Glu/Asp-rich domain within the 5A-1 clone is consistent with an expected negatively charged pocket capable of binding clonidine and agmatine, both of which are highly positively charged ligands. Furthermore, this stretch is located within the longest overall region of homology that the sequence has for any known protein, i.e., the ryanodine receptor (as determined by running EST04033 on BLAST). Specifically, we have discovered four regions of homology between the imidazoline receptor and the ryanodine receptor, which are all Glu/Asp-rich. In this region of the clone the total nucleic acid homology is 67% with the ryanodine receptor DNA sequence. However, this is not sufficient to indicate that the imidazoline receptor is a subtype of the ryanodine receptor, because the homologous sequence is still a minor portion of the 3318 bp sequence identified in the cloned cDNA. Instead, this significant homology may reflect a commonality in function between this region of the $IR_1$ and the ryanodine receptor.

The Glu/Asp-rich region within the ryanodine receptor, which is significantly homologous to clone 5A-1, has been reported to define a calcium and ruthenium red dye binding domain that modulates the ryanodine receptor/$Ca^{++}$ release channel located within sarcoplasmic reticulum. The only other charged amino acids within the Glu/Asp-rich region are two arginines (the ryanodine receptor has uncharged amino acids at the corresponding positions).

Based on the identification of Arg residues within the Glu/Asp-rich region of the predicted imidazoline binding site, the assistance of Dr. Paul Ernsberger (Case Western Reserve University, Cleveland, Ohio) was enlisted, who performed phenylglyoxal attack of arginine on native PC-12 membranes. Dr. Ernsberger was able to demonstrate that this treatment completely eliminated imidazoline binding sites in these membranes. This provided indirect evidence that the native imidazoline binding site also contains an Arg residue. Attempts to chemically modify cysteine and tyrosine residues, which are not located near the Glu/Asp-rich region did not affect PC-12 membrane binding.

As a further test of the sequence, it was determined whether native $IR_1$ binding sites in PC-12 cells would be sensitive to ruthenium red. Inasmuch as the cloned sequence had suggested a similarity with the ryanodine receptor in terms of ruthenium red binding, it was reasoned that native $IR_1$ should bind ruthenium red. Accordingly, a competition of ruthenium red with $^{125}$PIC at PC-12 $IR_1$ sites was studied. In these studies it was observed that ruthenium red competed for $^{125}$P1C binding equally well as did the potent imidazoline compound, moxonidine, i.e., 100% competition. Furthermore, the $IC_{50}$ for competition of ruthenium red at $IR_1$ was more robust than has been previously reported for ruthenium red on the activation of calcium-dependent cyclic nucleotide phosphodiesterase—indicating that it might have pharmacological importance. It is also noteworthy that calcium failed to compete for $^{125}$PIC binding at PC-12 $IR_1$ sites (as did a calcium substitute, lanthanum). We have previously reported that a number of other cations robustly interfere with $IR_1$ binding [Ernsberger et al., Annals NY Acad. Sci., 763: 22-42 (1995); Ernsberger et al., Annals NY Acad. Sci., 763: 163-168 (1995)]. Attempts were also made to directly stain the proteins in SDS gels with ruthenium red, and it was found that ruthenium red stains the same platelet (33 kDa) and brain (85 kDa) bands that Reis antiserum detects. That 33 kDa band was verified to directly correlate with $^{125}$PIC Bmax values for $IR_1$. Thus, these results strongly link the attributes predicted from the cloned sequence to a native $IR_1$ binding site.

Some additional findings about the amino acid sequence of an instant $IR_1$ polypeptide are: (1) it bears a similarity to an amino acid sequence within a GTPase activator protein; (2) it contains at least seven small hydrophobic domains indicative of seven transmembrane domain receptors; and (3) three potential protein kinase C (PKC) phosphorylation sites are near to the carboxy terminus, and we have previously found that treatment of membranes with PKC leads to an enhancement of native $IR_1$ binding. Thus, these observations are all consistent with the observations previously expected for $IR_1$.

Northern blotting has also been performed on polyA$^+$ mRNA from 22 human tissues in order to ascertain the regional expression of the mRNA corresponding to our cDNA. For these studies, a carboxy terminal coding sequence of clone 5A-1 (minus the Glu/Asp-rich region) was used as the labelled probe. This region was not found on any other known sequences on the BLASTN database. The results revealed a 6 kb mRNA band, which predominated over a much fainter 9.5 kb mRNA in most regions. The two exceptions to this pattern were in lymph nodes and cerebellum, where the 9.5 kb band was equally or more intense. In either case, the size of these mRNAs could easily encode a 70 kDa protein. Although the 6 kb band is weakly detectable in some non-CNS tissues, it is strikingly enriched in brain. An enrichment of the 6 kb mRNA is observed in brainstem, although not exclusively. Importantly, the regional distribution of the mRNA is generally in keeping with the known distribution of $IR_1$ binding sites, when extrapolated across species. Thus, the rank order of Bmax values for $IR_1$ in rat brain has been reported to be frontal cortex>hippocampus>medulla oblongata>cerebellum [Kamisaki et al., Brain Res., 514: 15-21 (1990)]. Therefore, with the exception of human cerebellum, which showed two mRNA bands, the distribution of the mRNA for the present cloned cDNA is consistent with it belonging to $IR_1$.

It should be noted that while $IR_1$ binding sites are widely considered to be low in cerebral cortex compared to brainstem, this is in fact a misinterpretation of the literature based only on comparisons to the alpha-2 adrenoceptort's Bmax, rather than on absolute values. Thus, $IR_1$ Bmax values have actually been reported to be slightly higher in the cortex than the brainstem, but they "appear" to be low in the cortex in comparison to the abundance of alpha-2 binding sites in cortex. Therefore, the distribution of the $IR_1$ mA is very much in keeping with the actual Bmax values for radioligand binding to the receptor [Kamisaki et al., (1990)].

Conclusion

A DNA molecule of the present invention expresses a protein that is immunoreactive with both of the known selective antisera for an imidazoline receptor, i.e., Reis antiserum and Dontenwill antiserum. Thus, an instant cDNA molecule produces a protein immunologically related to a purified imidazoline receptor and has the antigenic specificity expected for an imidazoline binding site. These antisera have been documented in the scientific literature as being selective for an "imidazoline receptor", which provides strong evidence that such an imidazoline receptor has indeed been cloned.

An instant cDNA sequence contains an open reading frame for a 70 kDa protein distinct from any previously described proteins having affinity for imidazoline compounds, i.e., the protein is not an $α_2$-adrenoceptor or monoamine oxidase. Also, at least seven small hydrophobic domains in the amino acid sequence corresponding to the DNA sequence have been identified, which suggests that the protein is probably membrane bound, as is expected for an imidazoline receptor. A short sequence homology was also observed with a domain in the human ryanodine receptor that encodes the ruthenium red binding site in the ryanodine receptor.

Further evidence that an $IR_1$ cDNA has been cloned is apparent from the fact that native $IR_1$ binding sites in PC-12 cells were found to be inhibited by ruthenium red dye. Moreover, ruthenium red was found to stain the protein band previously identified by us as the $IR_1$ protein in human platelets [Chen and MacLennan, J. Biol. Chem., 269: 22698-22704 (1994)]. Thus, based solely on our sequence we were able to predict that native imidazoline receptors would possess ruthenium red binding capacity, a finding that further establishes that an imidazoline receptor has indeed been cloned. A summary of this evidence that a cDNA encoding an imidazoline receptor (probably $IR_1$) protein has been cloned is summarized in the Table hereinbelow.

TABLE

Comparison of Properties of cDNA Clone with Properties of $IR_1$ and $I_2$ Sites

| Imidazoline Receptor-like clone | Authentic $IR_1$ | Authentic $I_2$ |
|---|---|---|
| λ phage fusion protein is immunoreactive with Dontenwill and Reis antiobodies | Dontenwill Ab inhibits RVLM $IR_1$ binding site ($^3$H-CLON) Reis Ab immunoreactivity correlates with platelet $IR_1$ Bmax ($^{125}$PIC). | Dentenwill & Reis Abs both inhibit brain $I_2$ site ($^3$H-IDX). |
| No G-Protein-binding consensus sequence; but similar to a GTPase | Weak-to-moderate sensitivity to GTP | Not sensitive to GTP |

TABLE-continued

Comparison of Properties of cDNA Clone with
Properties of $IR_1$ and $I_2$ Sites

| Imidazoline Receptor-like clone | Authentic $IR_1$ | Authentic $I_2$ |
|---|---|---|
| activator protein Predicts 70,000 MW protein | 85,000 MW immunoreactivity | 59-61,000 MW photoaffinity |
| Predicts 7 hydrophobic domains | Enriched in plasma membranes | Enriched in mitochondria |
| Encodes Glu/Asp-rich (negatively charged) domain consistent with $Ca^{++}$ and ruthenium red binding | Binds (+)-charged imidazolines Sensitive to divalent cations Sensitive to ruthenium red | Binds (+)-charged imidazolines Not sensitive to divalent cations Unknown sensitivity for Ru red |
| Arginine is only postively charged amino acid near Glu/Asp domain | Arg attack elimintaes binding Cys & Tyr attack w/o effect | Unknown |
| Encodes PKC sites | PKC treatment enhances binding | Unknown |
| Human mRNA Distribution; F. Cortex > hippocampus > medulla Transfected COS-7 cells have high affinity for moxonidine & p-iodoclonidine (PIC) | Rat $IR_1$ Bmax ($^{125}$PIC): F. Cortex > hippocampus > medulla High affinity for moxonidine and PIC | Rat $I_2$ Bmax ($^3$H-IDX): Medulla > F. Cortex Low affinity for moxonidine and PIC |

EXAMPLE 3

Transfection Studies

Figure 3:
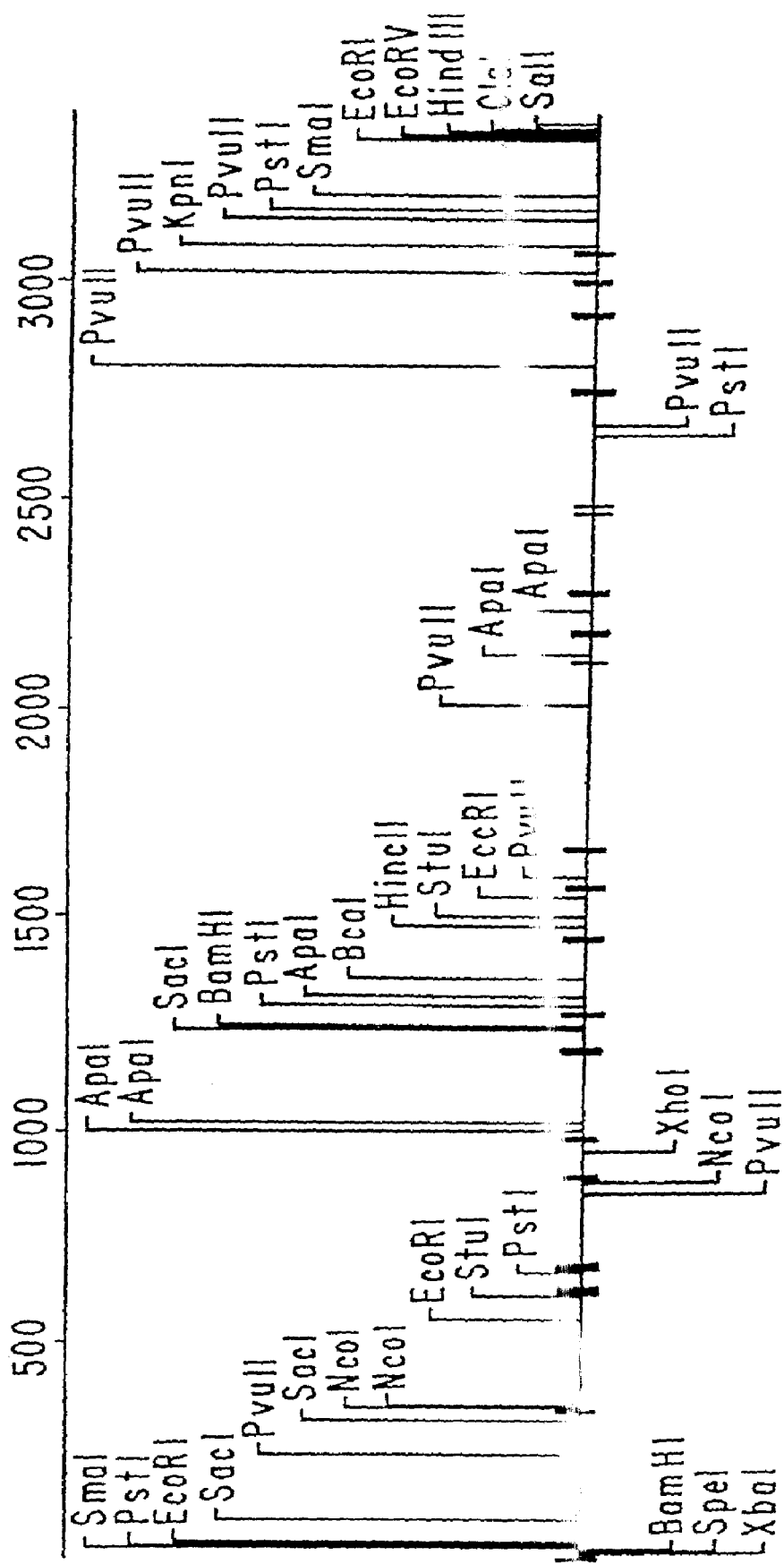
FIG. 3 depicts the restriction map of the IR$_1$ cDNA clone.

Transient transfection studies using the above-described full length EST04033 cDNA have been performed. COS-7 cells were transfected with a vector containing the EST04033 cDNA, which was predicted based on sequence analysis to contain the entire coding region of the imidazoline receptor protein, lacking only some 5' and 3' untranslated sequences. The EST04033 cDNA was subcloned into pSVK3 (Pharmacia LKB Biotechnology, Piscataway, N.J.) using standard techniques [Sambrook, supra], and transfected via the DEAE-dextran technique as previously described [Choudhary et al., *Mol. Pharmacol.*, 42: 627-633 (1992); Choudhary et al., *Mol. Pharmacol.*, 43: 557-561 (1993); Kohen et al., *J. Neurochem.*, 66: 47-56 (1996)]. A restriction map of the EST04033 cDNA is shown in FIG. 3. The restriction enzymes Sal I and Xba I were used for subcloning into pSVK3.

Briefly stated, COS-7 cells were seeded at 3 ×10$^6$ cells/100 mm plate, grown overnight and exposed to 2 ml of DEAE-dextran/plasmid mixture. After a 10-15 min. exposure, 20 ml of complete medium (10% fetal calf serum; 5 μg/ml streptomycin; 100 units/ml penicillin, high glucose, Dulbeccos' modified Eagle's medium) containing 80 μM chloroquine was added and the incubation continued for 2.5 hr. at 37° C. in a 5% $CO_2$ incubator. The mixture was then aspirated and 10 ml of complete medium containing 10% dimethyl sulfoxide was added with shaking for 150 seconds.

Following aspiration, 15 ml of complete medium with dialyzed serum was added and the incubation continued for an additional 65 hours. After this time period, the cells from 6 plates were harvested and membranes were prepared as previously described [Ernsberger et al., *Annals NY Acad. Sci.*, 763: 22-42 (1995), the disclosure of which is incorporated herein by reference]. Parent, untransfected COS-7 cells were prepared as a negative control. Some membranes were treated with and without PKC for 2 hrs prior to analysis, since previous studies had indicated that receptor phosphorylation could be beneficial to detect $IR_1$ binding.

The protocol used for Western blot assay of transfected cells is as follows. Cell membranes are prepared in a special cocktail of protease inhibitors (1 mM EDTA, 0.1 mM EGTA, 1 mM phenylmethyl-sufonylfluoride, 10 mM ε-aminocaproic acid, 0.1 mM benzamide, 0.1 mM benzamide-HCl, 0.1 mM phenanthroline, 10 μg/ml pepstatin A, 5 mM iodoacetamide, 10 μg/ml antipain, 10 μg/ml trypsin-chymotrypsin inhibitor, 10 pg/ml leupeptin, and 1.67 μg/ml calpain inhibitor) in 0.25 M sucrose, 1 MM $MgCl_2$, 5 mM Tris, pH 7.4. Fifteen μg of total protein are denatured and separated by SDS gel electrophoresis. Gels are equilibrated and electrotransferred to nitrocellulose membranes. Blots are then blocked with 10% milk in Tris-buffered saline with 0.1% Tween-20 (TBST) during 60 min. of gentle rocking. Afterwards, blots are incubated in anti-imidazoline receptor antiserum (1:3000 dil.) for 2 hours. Following the primary antibody, blots are washed and incubated with horseradish peroxidase-conjugated anti-rabbit goat IgG (1:3000 dil.) for 1 hr. Blots are extensively washed and incubated for 1 min. in a 1:1 mix of Amersham ECL detection solution. The blots are wrapped in cling-film (SARAN WRAP) and exposed to Hyperfilm-ECL (Amersham) for 2 minutes. Quantitation was based on densitometry using a standard curve of known amounts of protein containing BAC membranes or platelet membranes run in each gel.

One nM [$^{125}$I]p-iodoclonidine was employed as radioligand in the competition assays, since at this low concentration this radioligand is selective for the $IR_1$ site much more than for $I_2$ binding sites. The critical processes of membrane preparation of tissue culture cells and the radioligand binding assays of $IR_1$ and $I_2$ have recently been reviewed by Piletz and colleagues [Ernsberger et al., *Annals NY Acad. Sci.*, 763: 510-519 (1995)]. Total binding (n=12 per experiment) was determined in the absence of added competitive ligands and nonspecific binding was determined in the presence of 10$^{-4}$ M moxonidine (n=6 per experiment). Log normal competition curves were generated against unlabeled moxonidine, p-iodoclonidine, and (−) epinephrine. Each concentration of the competitors was determined in triplicate and the experiment was repeated thrice.

The protocol to fully characterize radioligand binding in the transfected cells entails the following. First, the presence of $IR_1$ and/or $I_2$ binding sites are scanned over a range of protein concentrations using a single concentration of [$^{125}$I]-p-iodoclonidine (1.0 nM) and $^3$H-idazoxan (8 nM), respectively. Then, rate of association binding experiments (under a 10 μM mask of NE to remove $\alpha_2$AR interference) are performed to determine if the kinetic parameters are similar to those reported for native imidazoline receptors [Ernsberger et al. *Annals NY Acad. Sci.*, 763: 163-168 (1995)]. Then, full Scatchard plots of [$^{125}$I]-p-iodoclonidine (2-20 nM if like $IR_1$) and $^3$H-idazoxan (5-60 nM if like $I_2$) binding are conducted under a 10 μM mask of NE. Total NE (10 μM)-displaceable binding is ascertained as a control to rule out $\alpha_2$-adrenergic binding. The Bmax and $K_D$ parameters for the transfected cells are ascertained by computer modeling using the LIGAND program [McPherson, G., *J. Pharmacol. Meth.*, 14: 213-228 (1985)] using 20 μM moxonidine to define $IR_1$ nonspecific binding, or 20 μM cirazoline to define $I_2$ nonspecific binding.

The results of the transient transfection experiments of the imidazoline receptor vector into COS-7 cells are shown in FIG. 4. Competition binding experiments were performed using membrane preparations from these cells and $^{125}$P1C was used to radiolabel I-sites. A mask of 10 μM norepinephrine was used to rule out any possible $\alpha_2 AR$ binding in each assay even though parent COS-7 cells lacked any $\alpha_2 AR$ sites. Moxonidine and p-iodoclondine (PIC) were the compounds tested for their affinity to the membranes of transfected cells. As can be seen, the affinities of these compounds in competition with $^{125}$PIC were well within the high affinity (nM) range.

The following $IC_{50}$ values and Hill slopes were obtained in this study: moxonidine, $IC_{50}$=45.1 nM (Hill slope=0.35±0.04); p-iodoclonidine without PKC pretreatment, $IC_{50}$=2.3 nM (Hill slope=0.42±0.06); p-iodoclonidine with PKC pretreatment, $IC_{50}$=19.0 nM (Hill slope=0.48±0.08). Shallow Hill slopes for [$^{125}$I]p-iodoclonidine have been reported before in studies of the interaction of moxonidine and p-iodoclonidine with the human platelet $IR_1$ binding site [Piletz and Sletten, (1993)]. Epinephrine failed to displace any of the [$^{125}$I]p-iodoclonidine binding in the transfected cells, as expected since this is a nonadrenergic imidazoline receptor. Furthermore, in untransfected cells less than 5% of the amount of displaceable binding was observed as for the transfected cells—and this "noise" in the parent cells all appeared to be low affinity (data not shown). These results thus demonstrate the high affinities of two imidazoline compounds, p-iodoclonidine and moxonidine for our cloned receptor. PKC pretreatment had no effect in the transfected COS cells.

It was also observed that the level of the expressed protein, as measured by immunoblotting of the transfected cells, was consistent with the level of $IR_1$ binding that was detected. Hence, the present results are in keeping with those expected for the native imidazoline receptor. In summary, these data provide direct evidence that the EST04033 clone encodes an imidazoline binding site having high affinities for moxonidine and p-iodoclonidine, which is expected for the $IR_1$ protein.

EXAMPLE 4

Stable Transfection Methods

Stable transfections can be obtained by subcloning the imidazoline receptor cDNA into a suitable expression vector, e.g., pRc/CMV (Invitrogen, San Diego, Calif.), which can then be used to transform host cells, e.g. CHO and HEK-293 cells, using the Lipofectin reagent (Gibco/BRL, Gaithersburg, Md.) according to the manufacturer's instructions. These two host cell lines can be used to increase the permanence of expression of an instant clone. The inventors have previously ascertained that parent CHO cells lack both alpha$_2$-adrenoceptor and $IR_1$ binding sites [Piletz et al., *J. Pharm.& Exper. Ther.*, 272: 581-587 (1995)], making them useful for these studies. Twenty-four hours after transfection, cells are split into culture dishes and grown in the presence of 600 μg/ml G418-supplemented complete medium (Gibco/BRL). The medium is changed every 3 days and clones surviving in G418 are isolated and expanded for further investigation.

EXAMPLE 5

Direct Cloning of Human Genomic IRK

Direct cloning from a human genomic library can be done by preparing labelled cDNA probes from different subcloned regions of our full-length cDNA and using the probes to screen a commercially available human brain genomic library. One genomic library is EMBL (Clontech), which integrates genomic fragments up to 22 kbp long. It is reasonable to expect that introns may exist within the human gene so that only by obtaining overlapping clones can the full gene be sequenced. A probe encompassing the 5' end of an instant cDNA is generally useful to obtain the gene promoter region. Clontech's Human PromoterFinder DNA Walking procedure provides a method for "walking" upstream or downstream from cloned sequences such as cDNAs into adjacent genomic DNA.

EXAMPLE 6

Methods for Preparing Antibodies to Imidazoline Receptive Proteins

An instant imidazoline receptive polypeptide can also be used to prepare antibodies immunoreactive therewith. Thus, transfected cell lines or other manipulations of the DNA sequence of an instant imidazoline receptor can provide a source of purified imidazoline receptor protein in sufficient quantities for immunization, which can lead to a source of selective antibodies having commercial value.

In addition, various kits for assaying imidazoline receptors can be developed that include either such antibodies or the purified imidazoline receptor protein. A purification protocol has already been published for the bovine imidazoline receptor in BAC cells [Wang et al, 1992] and an immunization protocol has also been published [Wang et al., 1993]. These same protocols can be utilized with little if any modification to afford purified human $IR_1$ protein and selective antibodies thereto.

In order to obtain antibodies to a subject peptide, the peptide may be linked to a suitable soluble carrier to which antibodies are unlikely to be encountered in human serum. Illustrative carriers include bovine serum albumin, keyhole limpet hemocyanin, and the like. The conjugated peptide is injected into a mouse, or other suitable animal, where an immune response is elicited. Monoclonal antibodies can be obtained from hybridomas formed by fusing spleen cells harvested from the animal and myeloma cells [see, e.g., Kohler and Milstein, *Nature*, 256: 495-497 (1975)].

Once an antibody is prepared (either polyclonal or monoclonal), procedures are well established in the literature, using other proteins, to develop either RIA or ELISA assays for imidazoline receptive protein [see, e.g., "Radioimmunoassay of Gut Regulatory Peptides; Methods in Laboratory Medicine," Vol. 2, chapters 1 and 2, Praeger Scientific Press, 1982]. In the case of RIA, the purified protein can also be radiolabelled and used as a radioactive antigen tracer.

Currently available methods to assay imidazoline receptors are unsuitable for routine clinical use, and therefore the development of an assay kit in this manner would have significant market appeal. Suitable assay techniques can employ polyclonal or monoclonal antibodies, as has been previously described [U.S. Pat. No. 4,376,110 (issued to David et al.), the disclosure of which is incorporated herein by reference].

SUMMARY

In summary, we have identified a unique cDNA sequence and have shown that it has the properties expected of an imidazoline receptor. Although two partial sequences of the entire sequence were found in public databases on the Internet, these are partial sequences (155-250 bp) and were not identified at all with respect to any encoded protein.

Moreover, neither of these sequences reliably defines any portion of the coding region for an instant IR$_1$ protein. The EST04033 clone, which was reported to contain the 155 bp sequence, was sequenced for the first time by the present inventors in its entirety (3318 bp) by the inventors. Prior to this, even the size of EST04033 was unknown. The present inventors also demonstrated that an imidazoline receptive site can be expressed in cells transfected with the entire cDNA clone, and this site has the proper potencies for an IR$_1$. Thus, a DNA sequence with an open reading frame for a 70 kDa human IR$_1$ protein has been identified from our clones and the amino acid sequence of the protein has been deduced. The authenticity of the expressed protein as that defining an IR$_1$ protein has been demonstrated in a variety of ways.

The present invention has been described with reference to specific examples for purposes of clarity and explanation. Certain obvious modifications of the invention readily apparent to one skilled in the art can be practiced within the scope of the appended claims.

What is claimed is:

1. A method of screening for a ligand of an imidazoline receptor as comprising:

culturing a host cell transfected with a vector comprising a nucleotide sequence encoding SEQ ID NO:7 operably linked with a promoter sequence in a culture medium to express an imidazoline receptive polypeptide encoded thereby;

contacting said polypeptide with a labeled ligand for the imidazoline receptor under conditions effective to bind the labeled ligand thereto; and detecting any displacement of the labeled ligand from said polypeptide, with displacement signifying that the candidate ligand is a ligand for the imidazoline receptor polypeptide.

2. The method of claim 1, wherein said contacting steps are performed on an intact cultured host cell.

3. The method of claim 1, further comprising isolating the cell membrane of said cultured host cell prior to performing said contacting steps.

4. The method of claim 1, wherein said contacting of said imidazoline receptor proteins with said candidate ligand is conducted at a plurality of candidate ligand concentrations.

5. The method of claim 1, wherein the labeled ligand is radiolabelled.

* * * * *